(12) United States Patent
von Segesser

(10) Patent No.: US 10,987,489 B2
(45) Date of Patent: Apr. 27, 2021

(54) STEERABLE GUIDE WIRE AND CATHETER WITH SHAPE CHANGE IN-SITU

(71) Applicant: Coraflo Ltd., Lausanne (CH)

(72) Inventor: Ludwig K. von Segesser, Lausanne (CH)

(73) Assignee: Coraflo Ltd., Lausanne (CH)

(*) Notice: Subject to any disclaimer, the term of this patent is extended or adjusted under 35 U.S.C. 154(b) by 367 days.

(21) Appl. No.: 15/901,598

(22) Filed: Feb. 21, 2018

(65) Prior Publication Data

US 2018/0243536 A1  Aug. 30, 2018

Related U.S. Application Data

(60) Provisional application No. 62/462,002, filed on Feb. 22, 2017.

(51) Int. Cl.
*A61M 25/01*    (2006.01)
*A61M 25/09*    (2006.01)
(Continued)

(52) U.S. Cl.
CPC .... *A61M 25/0147* (2013.01); *A61M 25/0905* (2013.01); *A61M 25/09025* (2013.01); *A61M 25/09041* (2013.01); *A61M 2025/0046* (2013.01); *A61M 2025/015* (2013.01); *A61M 2025/0293* (2013.01); *A61M 2025/09008* (2013.01); *A61M 2025/09083* (2013.01);
(Continued)

(58) Field of Classification Search
CPC ........... A61M 25/09; A61M 25/09025; A61M 25/09041; A61M 25/0102; A61M 25/0122; A61M 25/0133; A61M 25/0147; A61M 25/0152; A61M 25/0905; A61M 2025/0046; A61M 2025/015; A61M 2025/09083
See application file for complete search history.

(56) References Cited

U.S. PATENT DOCUMENTS 4,917,102 A * 4/1990 Miller ............. A61M 25/09025
                                                600/434
5,040,543 A * 8/1991 Badera ............ A61M 25/09025
                                                600/434
(Continued)

FOREIGN PATENT DOCUMENTS

DE          3625871 A1 * 2/1988 ........ A61M 25/0122
WO    WO-2010/119445 A1    10/2010
WO    WO-2014/087402 A1    6/2014

OTHER PUBLICATIONS

International Search Report dated Aug. 1, 2018, for PCT Application No. PCT/IB2018/051079, filed Feb. 21, 2018, 7 pages.
(Continued)

*Primary Examiner* — Daniel L Cerioni
(74) *Attorney, Agent, or Firm* — Mintz Levin Cohn Ferris Glovsky and Popeo, P.C.

(57) ABSTRACT

A steerable guide wire and/or a catheter device and associated method. The device includes a guide wire having a distal end, a hollow interior, and an anchoring mechanism positioned proximate to the distal end of the guide wire. The device further includes a core wire is slidably inserted into the hollow interior of the guide wire. Upon insertion, the core wire actuates the anchoring mechanism to anchor the guide wire at an anchoring location.

40 Claims, 25 Drawing Sheets

(51) Int. Cl.
*A61M 25/00* (2006.01)
*A61M 25/02* (2006.01)

(52) U.S. Cl.
CPC ............ *A61M 2025/09125* (2013.01); *A61M 2025/09183* (2013.01)

(56) References Cited

U.S. PATENT DOCUMENTS

| | | | | |
|---|---|---|---|---|
| 5,167,239 | A * | 12/1992 | Cohen | A61B 17/22032 |
| | | | | 600/434 |
| 8,753,312 | B2 * | 6/2014 | Bowe | A61M 25/0041 |
| | | | | 600/509 |
| 9,084,869 | B2 * | 7/2015 | Anderson | A61M 25/0041 |
| 9,242,068 | B2 * | 1/2016 | Thai | A61M 25/0021 |
| 9,314,591 | B2 * | 4/2016 | Ogle | A61M 25/01 |
| 9,387,308 | B2 * | 7/2016 | Hinchliffe | A61M 25/09 |
| 9,586,029 | B2 * | 3/2017 | Shekalim | A61M 25/09025 |
| 10,052,459 | B2 * | 8/2018 | Randolph | A61M 25/09 |
| 2002/0004644 | A1 * | 1/2002 | Koblish | A61B 18/1492 |
| | | | | 604/104 |
| 2002/0072689 | A1 * | 6/2002 | Klint | A61M 25/09025 |
| | | | | 600/585 |
| 2009/0076416 | A1 * | 3/2009 | Treacy | A61M 25/09025 |
| | | | | 600/585 |
| 2009/0198153 | A1 | 8/2009 | Shriver | |
| 2010/0268029 | A1 | 10/2010 | Phan et al. | |

OTHER PUBLICATIONS

Written Opinion dated Aug. 1, 2018, for PCT Application No. PCT/IB2018/051079, filed Feb. 21, 2018, 10 pages.

\* cited by examiner

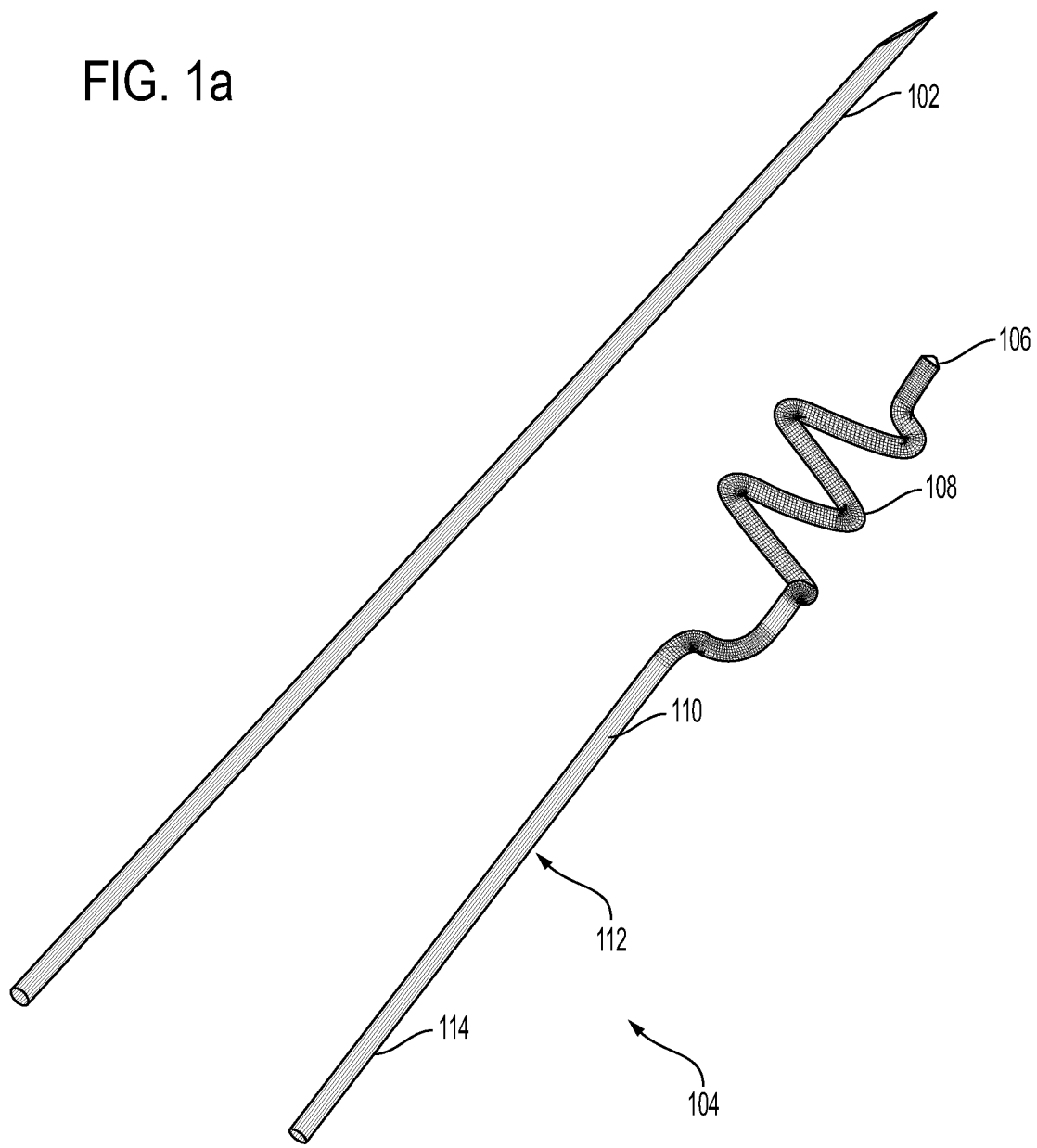

Experimental Results
035 ST guide wire traction with 2 narrow loops (radius 6 mm (=coil)) through 9.0 mm diameter tube

STEERABLE GUIDE WIRE AND CATHETER WITH SHAPE CHANGE IN-SITU

CROSS-REFERENCE TO RELATED APPLICATIONS

The present application claims priority to U.S. Provisional Patent Appl. No. 62/462,002 to von Segesser, filed Feb. 22, 2017, and entitled "Guide Wire With Shape Change In-Situ", and incorporates its disclosure herein by reference in its entirety.

TECHNICAL FIELD

In some implementations, the current subject generally relates to advancing and/or positioning of catheters, instruments, and/or other devices, and in particular to use of guide wire systems that are capable of changing shapes in-situ.

BACKGROUND

Guide wires are an essential requirement for insertion of catheters, instruments, and devices by the so-called Seldinger technique in diagnostic and therapeutic medical procedures. Some of the available guide wires include straight guide wires, curved guide wires, J-tip guide wires, ball tip guide wires, etc. The Seldinger technique can be referred to as the "catheter over the wire" technique. To allow a vascular access using this technique, a vessel is typically punctured using a hollow needle, adequate blood back flow is determined, and a guide wire is inserted through the hollow needle. Once the guide wire is positioned within the vessel, the hollow needle is removed, and a diagnostic and/or therapeutic catheter is inserted over the wire. The position of the catheter is controlled by fluoroscopy, ultrasonography and/or other suitable means. Finally, the guide wire is removed and the inserted, positioned catheter is used for its designated purpose. Alternatively, a device is inserted over the wire.

The Seldinger technique has been used for vascular access as well as multitude of other medical and non-medical fields, including angiology, cardiology, thoracic, cardio-vascular surgery radiology, urology, otorhinolaryngology, gastroenterology, etc. Thus, whenever a bodily organ (in particular, a hollow organ) has to be accessed for diagnostic and/or therapeutic procedures, the Seldinger technique is used. Use of a guide wire allows positioning of a number of devices, including catheters, balloons, micro-instruments, sophisticated diagnostic tools (e.g., intra-vascular ultrasound, intra-cardiac ultrasound, pressure probes etc.), therapeutic devices (e.g., intra-aortic balloons, cannulas for life support systems, stents, covered stents, stent grafts, catheter valves, pacemakers, pressure monitoring systems etc.), and/or any other devices.

However, some of the devices designed for insertion over the conventional guide wire are large compared to the dimensions of the access vessel and others are bulky making their insertion over a guide wire, positioning and unloading very difficult, even if a corresponding introducer catheter or wire has been positioned and the initial access has been mastered. To solve this problem, conventional techniques implement a larger and/or stiffer guide wire for the purposes of inserting a larger device. This technique suffers from inability to provide device insertion over a wire via tortuous access paths, e.g., contoured vessels, vessels with many narrow angles, etc. Angular paths can severely hamper control over the positioning of the guide wire tip from a remote location and decrease precision in advancing/positioning of the guide wire especially when narrower angles and/or serial angles are present in the path. One of the further problems using this approach is that a stiff or a larger device typically moves during insertion in the straightest possible direction disregarding a well-positioned guide wire that follows curvature of an access vessel. This can cause the tip of the guide wire to be pulled from the target position (i.e., the larger/stiffer device, because of its size/stiffness, advances using the largest possible radius of a curved access vessel). This can lead to vessel elongation, vessel rupture, a kinked guide wire, penetration of the vessel wall, and/or other problems. Hence, this prevents a successful completion of a planned procedure as well as can lead to adverse impacts to the patient.

To resolve the above issues, a conventional technique of a "through-and-through" guide wire, which allows for insertion of larger devices, is used. Here, a very long wire is inserted from, for example, the femoral artery into the ascending aorta, captured there with a lasso coming from the brachial or radial artery, and pulled through. During implantation of the covered stent graft, the "through-and-through" wire can be put under tension and straightened, which, in turn, helps during advancement of the device. Similar techniques have been used for a femoral venous access, puncture of the inter-atrial septum, passing through the mitral and the aortic valve in order to be captured from the femoral or the brachial artery for insertion of a catheter valve. Likewise, veno-venous, and arterio-venous paths are explored. Use of this technique can reduce the risk of wire kinks and facilitate insertion of the device. However, it is a complex procedure, and excessive wire traction as a result of this this technique can lead to complications.

SUMMARY

In some implementations, the current subject matter relates to a guide wire system and a method for implanting a medical device. The guide wire system can include a core wire slidably inserted into a guide wire. The guide wire can have a hollow interior that can accommodate insertion and/or sliding of the core wire. The core wire can include a distal end, which can be farthest from the user of the guide wire system and proximate to the anchoring location of the guide wire, and a proximate end, which is closest to the user of the guider system. The guide wire can also include a distal end and a proximate end that can substantially coincide with the distal and proximate ends of the core wire, respectively, where the distal end of the guide wire can include a tip. The distal end of the core wire can be coupled to the distal end or the tip of guide wire. The guide wire can include an anchoring mechanism that can be disposed proximate to the tip of the guide wire. The core wire can be used to activate and/or deactivate the anchoring mechanism. The core wire can include an actuation mechanism (e.g., a catheter, etc.) that can be disposed at a proximate end of the core wire (and/or at any other suitable location) that can be used to activate and/or deactivate the anchoring mechanism. Alternatively, the current subject matter's guide wire can be released from a catheter for activation of the anchoring mechanism.

The anchoring mechanism can be used to anchor the guide wire at a location that can be adjacent to a target location (e.g., a location where delivery of a medical device (e.g., catheter, stent, etc.) is desired) and/or at the target location. The anchoring mechanism can have a contracted state and an expanded state. In a contracted state, the guide wire can be configured for insertion into the target location as well as removal of the guide wire (e.g., after implantation of the device and/or for the purposes of re-anchoring, etc.). In an expanded state, the anchoring mechanism can be activated and can secure (e.g., by friction fitting, or anchoring in any other fashion) the guide wire proximate to and/or at the target location. In the expanded state, the portion of the guide wire that extends from the guide wire's proximate end to the section of the guide wire that connects to the anchoring mechanism can be appropriately tensioned so that delivery and/or implantation of the device can occur.

In some implementations, to deliver/implant a medical device, the guide wire can be delivered with its anchoring mechanism in a contracted state to the location that is adjacent to the target location and/or to the target location (hereinafter, referred to as an "anchoring location"). The anchoring location can be a location that is beyond the target location, and thus, the guide wire can be advanced past the target location and into the anchoring location. Once at the anchoring location, the anchoring mechanism can be activated using the core wire to transform the anchoring mechanism into the expanded state. In some implementations, at least one dimension of the expanded state can be greater than at least one dimension of an interior portion of the anchoring location. In the expanded state, the anchoring mechanism can form a friction fit and/or form fit with the anchoring location, thereby securing the guide wire to the anchoring location and allowing delivery/implantation of the medical device along the guide wire.

In some implementations, the anchoring mechanism can include coils, angles, Z-shapes or zig-zag shapes, etc., which can have two and/or three dimensions, and/or any combinations thereof. In some implementations, the anchoring mechanism can include a basket, a ball, an ovoid, a diabolo, a cylinder, a cone, an inverted cone, a pyramid, and/or any other shapes, and/or any combinations thereof. Further, the anchoring mechanism can include a ball or a plug, a covered ball, a plug with a waist, a covered plug with a waist, a cone, an inverted cone, a dual accordion, a triple accordion, a multiple-accordion structure, a torus, and/or any other shapes, and/or any combinations thereof. In some implementations, the anchoring mechanism can further include pins, hooks, screw, a balloon, and/or any other mechanism, and/or any combinations thereof.

In some implementations, the guide wire can include a navigation section (e.g., the tip of the guide wire), an anchoring section (e.g., the anchoring mechanism), a device implantation section, a device transfer section, and a steering section. The navigation section can be located at the distal end of the guide wire and the steering section can be located proximate to the user of the current subject matter's guide wire system. The navigation section can be used to navigate the guide wire to the target location and beyond (e.g., for anchoring purposes). The anchoring section, as discussed above, can be used to anchor the guide wire at the anchoring location (e.g., the target location and/or beyond the target location). The device implantation section can allow for implantation of the device, which can be delivered over the guide wire, at the target location. The device transfer section can be used for transferring the device to the device implantation section for implantation. The steering section can allow the user of the guide wire system to steer the guide wire to the anchoring and/or target locations. Upon actuation of the anchoring mechanism, the guide wire can form one or more angles between the anchoring section and the device implantation section. In some implementations, smaller angle(s) can allow for an improved anchoring of the anchoring section, while larger angle(s) can allow for easier removal of the guide wire.

In some implementations, the current subject matter relates to a device (e.g., a guide wire and/or a catheter) that can include a guide wire having a distal end, a hollow interior, and an anchoring mechanism positioned proximate to the distal end of the guide wire. In some implementations, the guide wire may or may not have a hollow interior. The device can further include a core wire configured to be slidably inserted into the hollow interior of the guide wire and, upon insertion, configured to actuate the anchoring mechanism to anchor the guide wire at an anchoring location.

In some implementations, the current subject matter can include one or more of the following optional features. The core wire can include a distal end, where the distal end of the core wire can be configured to be positioned proximate to the anchoring location of the guide wire and proximate to the distal end of the guide wire.

In some implementations, the guide wire can include a tip at the distal end of the guide wire. The distal end of the core wire can be configured to be coupled to at least one of the distal end guide wire and the tip of guide wire.

In some implementations, the core wire can be configured to deactivate the anchoring mechanism for removing of the guidewire from the anchoring location. The core wire can include an actuation mechanism disposed at a proximate end of the core wire. The actuation mechanism can be configured to perform activation and deactivation of the anchoring mechanism.

In some implementations, the anchoring location can include at least one of the following: a target location for delivery of a medical device or a procedure, a location proximate to the target location, and any combination thereof. The anchoring mechanism can include at least one of a contracted state and an expanded state. In the contracted state, the guide wire can be configured for at least one of an insertion into the target location and removal of the guide wire from the target location. In the expanded state, the anchoring mechanism can be configured to be activated and can be further configured to secure the guide wire at at least one of proximate to the target location and at the target location. Further, in the expanded state, a first section of the guide wire extending from a proximate end of the guide wire to a second section of the guide wire that connects to the anchoring mechanism can be configured to be tensioned.

In some implementations, the anchoring mechanism can include at least one of the following: a coil, an angle, a Z-shape, a zig-zag shape, and any combination thereof.

In some implementations, the anchoring mechanism can be at least one of a two-dimensional anchoring mechanism configured to anchor the guide wire at the anchoring location in at least two dimensions, and a three-dimensional anchoring mechanism configured to anchor the guide wire at the anchoring location in at least three dimensions.

In some implementations, the anchoring mechanism can include at least one of the following: a basket, a ball, an ovoid, a diabolo, a cylinder, a cone, an inverted cone, a pyramid, a screw, one or several directional nozzles, a suction cup and/or any other shapes, and/or any combinations thereof.

In some implementations, the anchoring mechanism can include at least one of the following: a ball or a plug, a covered ball, a plug with a waist, a covered plug with a waist, a cone, an inverted cone, a dual accordion, a triple accordion, a multiple-accordion structure, a torus, and/or any other shapes, and/or any combinations thereof.

In some implementations, the anchoring mechanism can include at least one of the following: a pin, a hook, a balloon, and/or any combinations thereof.

In some implementations, the guide wire can include a navigation section, the anchoring mechanism, a device transfer section, a device implantation section, and a steering section. The navigation section can be configured to be located proximate to the distal end of the guide wire and is further configured to navigate the guide wire to at least a target location. The anchoring mechanism can be configured to be located adjacent to the navigation section. The device transfer section can be configured to be located adjacent to the anchoring mechanism and can be further configured to transfer a medical device to the device implantation section for implantation. The medical device can be configured to be delivered over the guide wire to the target location. The device implantation section can be configured to be located adjacent to the device transfer section and can be further configured for implantation of the medical device at the target location. The steering section can be configured to be located proximate to the proximate end of the guide wire.

In some implementations, upon actuation of the anchoring mechanism, the guide wire can be configured to form at least one angle between the anchoring section and the device implantation section. The anchoring mechanism can be configured to anchor the guide wire at the anchoring location using at least one of the following: a friction fit, a form fit, an active fixation, a permanent fixation, a temporary fixation, and any combination thereof. The anchoring mechanism can be also configured to anchor the guide wire at the anchoring location using at least one of the following: an automatic anchoring, a manual anchoring, and any combination thereof.

In some implementations, the anchoring mechanism can include at least one steering mechanism for at least one of: dynamically moving, steering, positioning, stabilization, and anchoring of the guide wire to at least the anchoring location. The steering mechanism can include at least one nozzle configured to provide a conduit between the hollow interior of the guide wire and an exterior of the guide wire. At least one nozzle can be configured to be actuated using at least one of: the core wire and a pressure applied from the hollow interior of the guide wire, wherein the pressure is applied using at least one substance. Upon actuation, the nozzle can be configured to expunge the at least one substance from the hollow interior of the guide wire to perform at least one of: movement, steering, positioning, stabilization, and anchoring of the guide wire. The nozzle can be configured to be positioned proximate to the distal end of the guide wire. The substance can include at least one of the following: a fluid substance, a gaseous substance, an amorphous substance, a solid substance, and any combination thereof.

In some implementations, the guide wire can be a catheter configured to be at least one of: dynamically moved, steered, positioned, stabilized, and anchored at a predetermined location for performing at least one diagnostic procedure and a therapeutic procedure.

In some implementations, the current subject matter relates to a method. The method can include providing a guide wire having a distal end, a hollow interior, and an anchoring mechanism positioned proximate to the distal end of the guide wire, and a core wire configured to be slidably inserted into the hollow interior of the guide wire and, upon insertion, configured to actuate the anchoring mechanism to anchor the guide wire at an anchoring location; delivering the guide wire to the anchoring location; and anchoring, using the core wire, the guide wire at the anchoring location.

In some implementations, the current subject matter relates to a method for using a guide wire (as for example, discussed herein). The method can include providing a guide wire having a distal end, a hollow lumen, and an anchoring mechanism positioned proximate to the distal end of the guide wire, actuating the anchoring mechanism by pressurizing at least one substance inside the hollow lumen, and performing, using the actuated anchoring mechanism, at least one of the following functions: advance the guide wire in a desired direction, anchor the guide wire at an anchoring location, steer the guide wire in a desired direction, position the guide wire at a predetermined location, stabilize the guide wire at a predetermined location and any combination thereof.

In some implementations, the current subject matter can include one or more of the following optional features (in addition to the features described herein). The anchoring mechanism can include at least one nozzle configured to provide a conduit between the hollow lumen of the guide wire and an exterior of the guide wire. The nozzle can be configured to be actuated using at least one of: a core wire and a pressure applied from the hollow lumen of the guide wire, wherein the pressure is applied using at least one substance. Upon actuation, the nozzle can be configured to expunge the substance from the hollow interior of the guide wire to perform at least one of: movement, steering, positioning, stabilization, and anchoring of the guide wire. The substance can include at least one of the following: a fluid substance (e.g., saline, therapeutic fluid, etc.), a gaseous substance (e.g., air, gas, etc.), an amorphous substance (e.g., a combination of fluids, gases, solids, etc.), a solid substance (e.g., a metal, etc.), and any combination thereof. The nozzle can be configured to be positioned proximate to the distal end of the guide wire. In some implementations, the guide wire can be a catheter for performing at least one of a diagnostic procedure and a therapeutic procedure.

In some implementations, the current subject matter relates to a method of using a guide wire (such as a guide wire discussed herein). The method can include providing a guide wire having a distal end and an anchoring mechanism positioned proximate to the distal end of the guide wire. The anchoring mechanism can have a first configuration (e.g., a contracted state, as discussed above) for delivery of the guide wire to an anchoring location, and a second configuration (e.g., an expanded state, as discussed above) for anchoring of the guide wire at the anchoring location. The first configuration can have at least one dimension smaller than at least one dimension of the anchoring location (e.g., the guide wire can be stretched for delivery of the guide wire and hence be smaller than a diameter of a vessel to where it is being delivered). The second configuration can have at least one dimension larger (e.g., in the expanded state, the guide wire have its anchoring section be larger than a diameter of a vessel where the guide wire is being delivered to) than at least one dimension of the anchoring location. The method can also include delivering the guide wire to the anchoring location, actuating the anchoring mechanism, where the anchoring mechanism can be configured to assume the second configuration, and anchoring the guide wire at the anchoring location.

In some implementations, the current subject matter can include one or more of the following optional features. The anchoring location can include at least one of the following:

a target location for delivery of a medical device or a procedure, a location proximate to the target location, and any combination thereof.

In some implementations, the first configuration can correspond to an expanded state of the guide wire, where, in the expanded state, a first section of the guide wire extending from a proximate end of the guide wire to a second section of the guide wire that connects to the anchoring mechanism is configured to be tensioned.

In some implementations, the anchoring mechanism can include at least one of the following: a coil, an angle, a Z-shape, a zig-zag shape, and any combination thereof. The anchoring mechanism can be at least one of a two-dimensional anchoring mechanism configured to anchor the guide wire at the anchoring location in at least two dimensions, and a three-dimensional anchoring mechanism configured to anchor the guide wire at the anchoring location in at least three dimensions. The anchoring mechanism can include at least one of the following: a basket, a ball, an ovoid, a diabolo, a cylinder, a cone, an inverted cone, a pyramid, a screw, one or several directional nozzles, a suction cup and/or any other shapes, and/or any combinations thereof. The anchoring mechanism can include at least one of the following: a ball or a plug, a covered ball, a plug with a waist, a covered plug with a waist, a cone, an inverted cone, a dual accordion, a triple accordion, a multiple-accordion structure, a torus, and/or any other shapes, and/or any combinations thereof. The anchoring mechanism can also include at least one of the following: a pin, a hook, a balloon, and/or any combinations thereof.

In some implementations, upon actuation of the anchoring mechanism, the guide wire can be configured to form at least one angle.

In some implementations, the anchoring mechanism can be configured to anchor the guide wire at the anchoring location using at least one of the following: a friction fit, a form fit, an active fixation, a permanent fixation, a temporary fixation, and any combination thereof. The anchoring mechanism can be further configured to anchor the guide wire at the anchoring location using at least one of the following: an automatic anchoring, a manual anchoring, and any combination thereof.

In some implementations, a sheathing device (e.g., a catheter, and/or any other sheathing device, etc.) can be provided to sheath the guide wire for delivery of the guide wire to the anchoring location in the first configuration. Upon removal of the sheathing device, the guide wire can be configured to assume the second configuration.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings, FIG. 1a illustrates a conventional guide wire and an exemplary guide wire system, according to some implementations of the current subject matter;

DETAILED DESCRIPTION

Figure 1B:
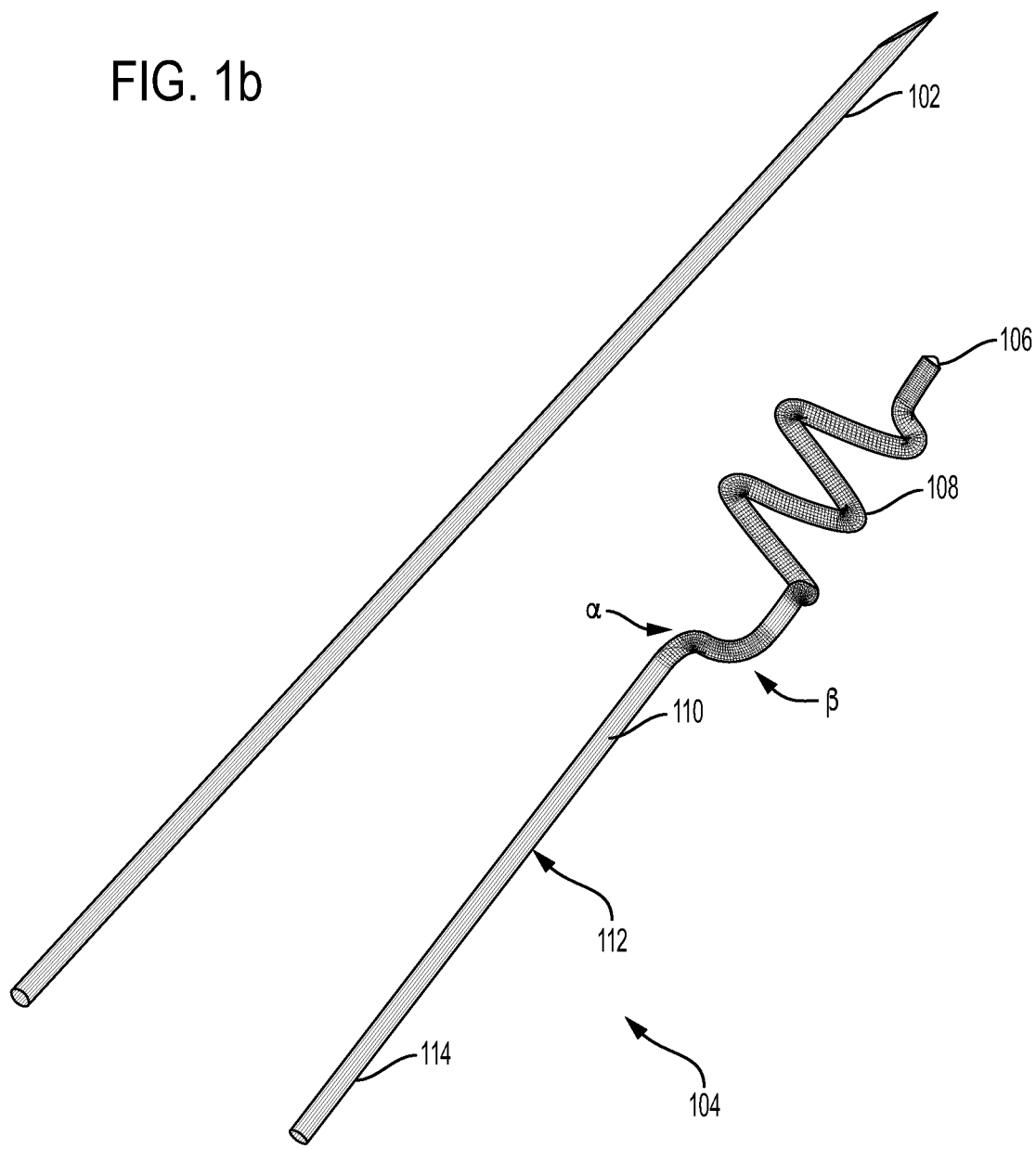
FIG. 1b illustrates additional views of a conventional guide wire and an exemplary guide wire system, according to some implementations of the current subject matter.

To address deficiencies of some of the existing guide wire designs and techniques, some exemplary implementations of the current subject matter provide for an improved guide wire system and associated techniques for insertion, advancement and/or placement, as well as implantation/delivery of a medical device.

In some implementations, the current subject matter relates to a guide wire system. The guide wire system can include a guide wire having a hollow interior and core wire that can (and/or may not) be slidably inserted and/or movable in the hollow interior of the guide wire (alternatively, and/or in addition to, the core wire can be slidably inserted and/or movable over portions and/or segments of the guide wire and/or the entire guide wire). The guide wire can have a distal end or a tip or a zone that is substantially near the guide wire's endpoint and that can be located farthest from the user when the guide wire is being used. The guide wire can include a navigation section (e.g., the tip of the guide wire), an anchoring or traction section (e.g., which can include an anchoring mechanism), a device implantation section, a device transfer section, and a steering section. The terms "traction" and "anchor"/"anchoring" will be used interchangeably throughout the present description, whereby the current subject matter's guide wire system is configured to provide an increased traction to and/or stabilize the guide wire (e.g., through friction and/or form fitting, as discussed below) once the guide wire has been advanced to/positioned at the desired location within the body of the subject. This is in contrast to the conventional guide wires that are not capable of providing traction and/or stabilization of the guide wires.

The navigation section can be located at the distal end of the guide wire and the steering section can be located proximate to the user of the current subject matter's guide wire system. The navigation section can be used to navigate the guide wire to the target location and/or beyond (e.g., for anchoring purposes).

The anchoring section can be used to anchor the guide wire at an anchoring location (e.g., the target location and/or beyond the target location). This can be accomplished through friction fitting and/or form fitting and/or screwing, as discussed below.

The device implantation section can allow for implantation of the device, which can be delivered over the guide wire, at the target location. The device transfer section can be used for transferring the device to the device implantation section for implantation. The steering section can allow the user of the guide wire system to steer the guide wire to the anchoring and/or target locations.

In some implementations, the anchoring section can be disposed proximate to the tip of the guide wire. The anchoring section can be configured to change its configuration and/or geometry in-situ, e.g., at the target location and/or any other desired location. The changed configuration can provide friction and/or form fitting of the guide wire at the anchoring location. The target location can correspond to a location where implantation of a medical device (e.g., a catheter, a stent, a cannula, valve, etc.) can be desired. Exemplary locations can include arteries, veins, and/or any other vessels, organs (e.g., parenchymatous organs), cavities, openings, etc. in the body of a subject.

The configuration/geometry of the anchoring section can be changed between an expanded state and a contracted state. In the contracted state, the guide wire can be inserted to the target location and/or beyond the target location (hereinafter, referred as the "anchoring location") as well as can be removed (e.g., once device implantation is complete and/or for re-anchoring purposes). In the expanded state, the anchoring section can be expanded (e.g., by pulling on a core wire and/or by releasing it from a guiding catheter) to create a friction fit and/or a form fit (and/or any other anchoring fit) between an interior wall of the anchoring location and the anchoring section of the guide wire. In the expanded state, the guide wire cannot be easily withdrawn from the anchoring location and can allow for delivery of the device to the target location. In some implementations, the guide wire can be straightened to ease delivery of the device to the target location. The configuration/geometry of the anchoring section can be altered so that it can be larger than dimension(s) of the anchoring location (e.g., dimensions (e.g., diameter, etc.) of the vessel, organ, cavity, opening, etc. where the guide wire is being positioned (e.g., through friction fit, form fit, and/or any other fit)). Hence, the configuration/geometry of the guide wire can be reversibly altered in situ when the guide wire is advanced to the anchoring location. In some implementations, the anchoring section of the guide wire can be changed to a plurality of shapes/configurations, including but not limited to, loops, spirals, coils, curls, Z-shaped forms, cylinders, baskets, etc., as will be discussed below.

In some implementations, when the anchoring mechanism is actuated, the guide wire can form one or more angles between the anchoring section and the device implantation section. In some implementations, smaller angle(s) can allow for an improved anchoring of the anchoring section, which may make it more difficult to remove the guide wire, thereby increasing anchoring stability of the guide wire in the expanded state. Larger angle(s) can allow for easier removal of the guide wire, however, anchoring stability of the guide wire in the expanded state may be reduced. The angles can be angles that may be suitable for the purposes of delivery/implantation of the medical device.

In some implementations, as stated above, the exemplary guide wire can include a navigation section or zone, an anchoring section or zone, a device implantation section or zone, a device transfer section or zone, and a steering section or zone. The current subject matter's guide wire provides for an increased stability of the guide wire once the guide wire has been advanced to the anchoring location and its anchoring section is placed into an expanded state. The expanded state of the anchoring section can allow for an increased friction between anchoring section and the anchoring location (e.g., interior walls of the vessel, organ, cavity, opening, etc. where anchoring is performed). The increased friction can allow for an increased traction of the guide wire, which, in turn, can improve insertion of devices and/or prevent movement of the guide wire once it is being used for insertion of the devices (whether or not the guide wire has been positioned at a target location).

In some exemplary implementations, to overcome difficulties that can be associated with guide wire insertion, a larger, oversized exchange catheter can be positioned over a soft guide wire in the anchoring location (e.g., zone beyond the target location used for implantation). The guide wire can be designed for traction and can then be safely brought in the right position and unsheathed there. The exchange catheter can then be removed and the device can be implanted over the guide wire after putting the latter under traction in order to achieve an implantation path as straight as possible. Once the device is implanted over the guide wire designed for being put under traction during the implantation procedure, the traction guide wire can be re-sheathed using the oversized catheter or a device delivery catheter, and removed with or without the catheter. In some implementations, a device carrying catheter can be used for the purposes of withdrawal/removal.

The guide wire navigation section can be a tip of the guide wire. The tip can be straight, curved, J-type and/or any other desired configuration. The tip can be configured for ease of insertion, visualization, reduction of trauma, and/or any other purposes. The navigation section can have various degrees of stiffness, which can be a function of the intended use of the guide wire, target location, and/or any other factors. In some implementations, the current subject matter can allow for straightening the tip of the guide wire (if necessary or desired) along with any other sections of the guide wire. The straightening may be used for the purposes of preventing perforation and/or circumventing obstacles (e.g., during insertion of the guide wire) without perforation of tissue.

In some implementations, the current subject matter, in contrast to conventional systems, can provide requisite traction for the guide wire (e.g., once the guide wire has been inserted and advanced to the anchoring location) and can further secure positioning of the device implantation section and/or the device transfer section of the guide wire so that delivery/implantation of the device can occur. This is also in contrast to conventional systems that require anchoring of the guide wire outside of the body of the subject.

The guide wire's anchoring section can be located between the navigation section and the device implantation section. The anchoring section can include various means to increase friction between the guide wire and the anchoring location to keep the guide wire in place when traction is applied for straightening. In alternate exemplary implementations, the guide wire's anchoring section can be designed to have a form that can fit the intended anchoring location. In some exemplary implementations, the anchoring section can have a self-reconfiguring design (e.g., memory shape material, thermo-sensitive nitinol, non-thermo-sensitive nitinol, stainless steel, polyester, etc., and/or any combination thereof), which can be stretched using a straightening catheter. Upon insertion of the guide wire (which can be sheathed) to the anchoring location, the catheter can be removed or pulled back, thereby unsheathing the guide wire's anchoring section. Once unsheathed, the anchoring section can automatically expand into an expanded state to create a friction fit with the interior of the anchoring location. The expanded state of the anchoring section can be designed to be larger than the interior dimensions of the anchoring location. Additionally, in some exemplary implementations, the current subject matter can implement a preformed guide wire section that can adopt a specific configuration during positioning and/or during transfer of a device, which can result in superior procedure results.

In some implementations, the anchoring section (in an expanded state) can have at least one of the following shapes: coils, angles, Z-shapes or zig-zag shapes, etc. in two or three dimensions, and/or any combinations thereof. The shapes can be active and/or passive, permanent and/or temporary, etc., and/or any combination thereof. The shapes can also have various configurations, e.g., baskets, balloons, pyramids, screws, etc., and/or any combination thereof. Additionally, the anchoring section can also have various surface treatments that can increase friction and/or anchoring, including but not limited to, specific coatings, knobs, ribs, spikes, hooks, secondary coils etc., and/or any combination thereof. The surface treatments can be entirely, partially and/or otherwise be sheathed and re-sheathed during implantation procedure. Further, the anchoring section can also have various degrees of guide wire stiffness. The degrees of stiffness can be determined as a function of the intended guide wire configuration and/or use during insertion and/or during traction as well as the planned traction forces, the expected target site specifications, re-sheathing and/or removal forces for removal of the guide wire, and/or any combination thereof.

The device implantation section can be a section of the guide wire following the anchoring section (e.g., as viewed from the tip of the guide wire). It can also be a section of the guide wire up to which the device to be implanted can be advanced. The exterior surface of the implantation section of the guide wire can be smooth (e.g., as smooth as possible). This section may or may not include specific coating(s) for ease of adjustment of the device positioning during the device implantation procedure. Further, the implantation section can also have various degrees of guide wire stiffness. The degrees of stiffness of the implantation section can be determined as a function of the device being implanted, intended implantation path, intended guide wire configuration and/or use during insertion and/or during traction as well as the planned traction forces, the expected target site specifications, re-sheathing and/or removal forces for removal of the guide wire, and/or any combination thereof.

In some implementations, upon actuation of the anchoring section into the expanded state, the guide wire can form one or more angles between the device implantation section and the anchoring section. In some implementations, smaller angle(s) can allow for an improved anchoring of the anchoring section, while larger angle(s) can allow for easier removal of the guide wire.

The device transfer section of the guide wire can be located between implantation section and the guide wire steering section (e.g., the latter being farthest away from the tip of the guide wire). The exterior surface of the transfer section can also be smooth (e.g., as smooth as possible). It may or may not have specific coating(s), which can be used for the purposes of improving transfer of the device to be implanted from outside of the patient's body and into the body up to the implantation section of the guide wire. The transfer section can also have various degrees of guide wire stiffness. Likewise, the degrees of stiffness of the transfer section can be determined as a function of the device being implanted, intended implantation path, intended guide wire configuration and/or use during insertion and/or during traction as well as the planned traction forces, the expected target site specifications, re-sheathing and/or removal forces for removal of the guide wire, and/or any combination thereof. Further, various preformed shapes of one or more guide wire sections are possible. For example, pre-forming can be possible by having permanent and/or temporary shapes of one or more sections of the guide wire (e.g., through use of shape-memory materials and/or in any other desired fashion).

The steering section can be located at a proximal to the end of the guide wire and opposite to the tip of the guide wire. The steering section may or may not be blunt. It can allow for easy loading of catheters and/or devices with the corresponding lumen(s). The steering section can also have a section where a core wire can be accessible. The core wire can be slidably inserted into and/or through the hollow interior of the guide wire. This can allow for remote control of the anchoring section of the guide wire. Axial movement of the core wire with reference to the guide wire coil, tube, and/or body (which can be segmented or not) can activated using two and/or three dimensional structures that can be incorporated into the anchoring section of the guide wire. An exemplary conventional solid guide wire and a conventional coated guide wire coiled on a core wire are shown in FIG. 1e, whereas a guide wire made from a segmented tube 150 (as, for example, available from Boston Scientific, Marlborough, Mass., USA) as shown in FIG. 1d.

Figure 1C:
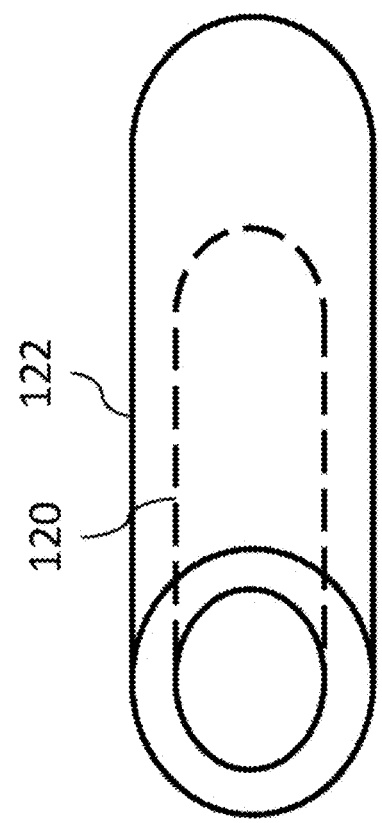
FIG. 1c illustrates cross-sectional views of an exemplary guide wire system, according to some implementations of the current subject matter.
Figure 1C:
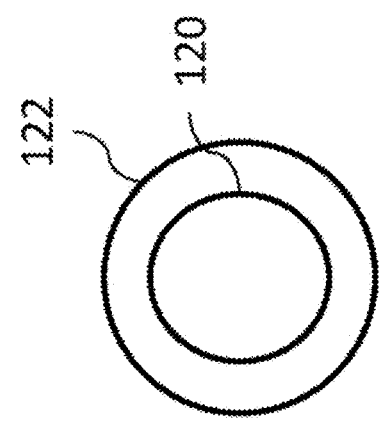
Figure 1D:
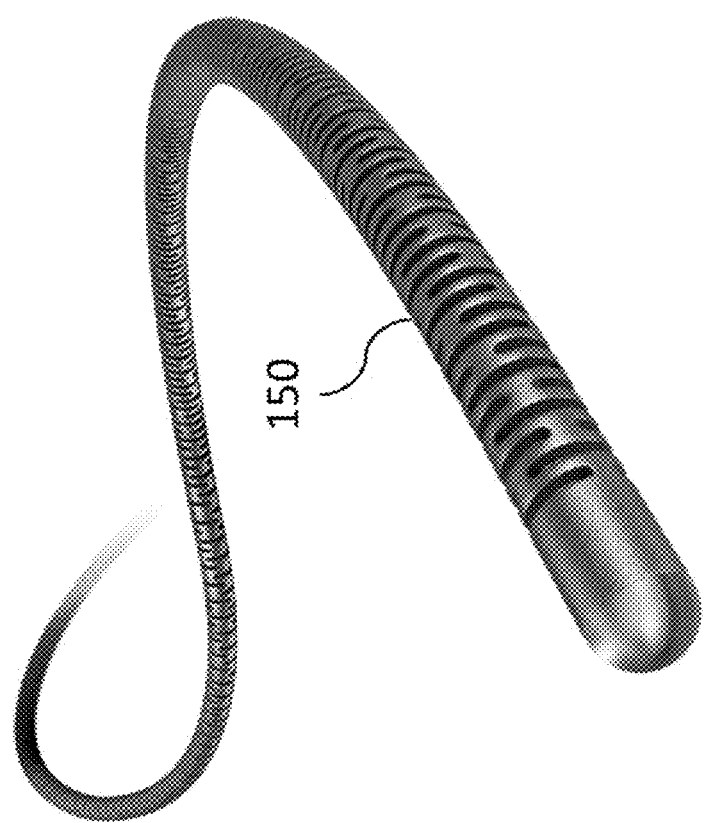
FIG. 1d illustrates a guide wire manufactured from a segmented tube.
Figure 1E:
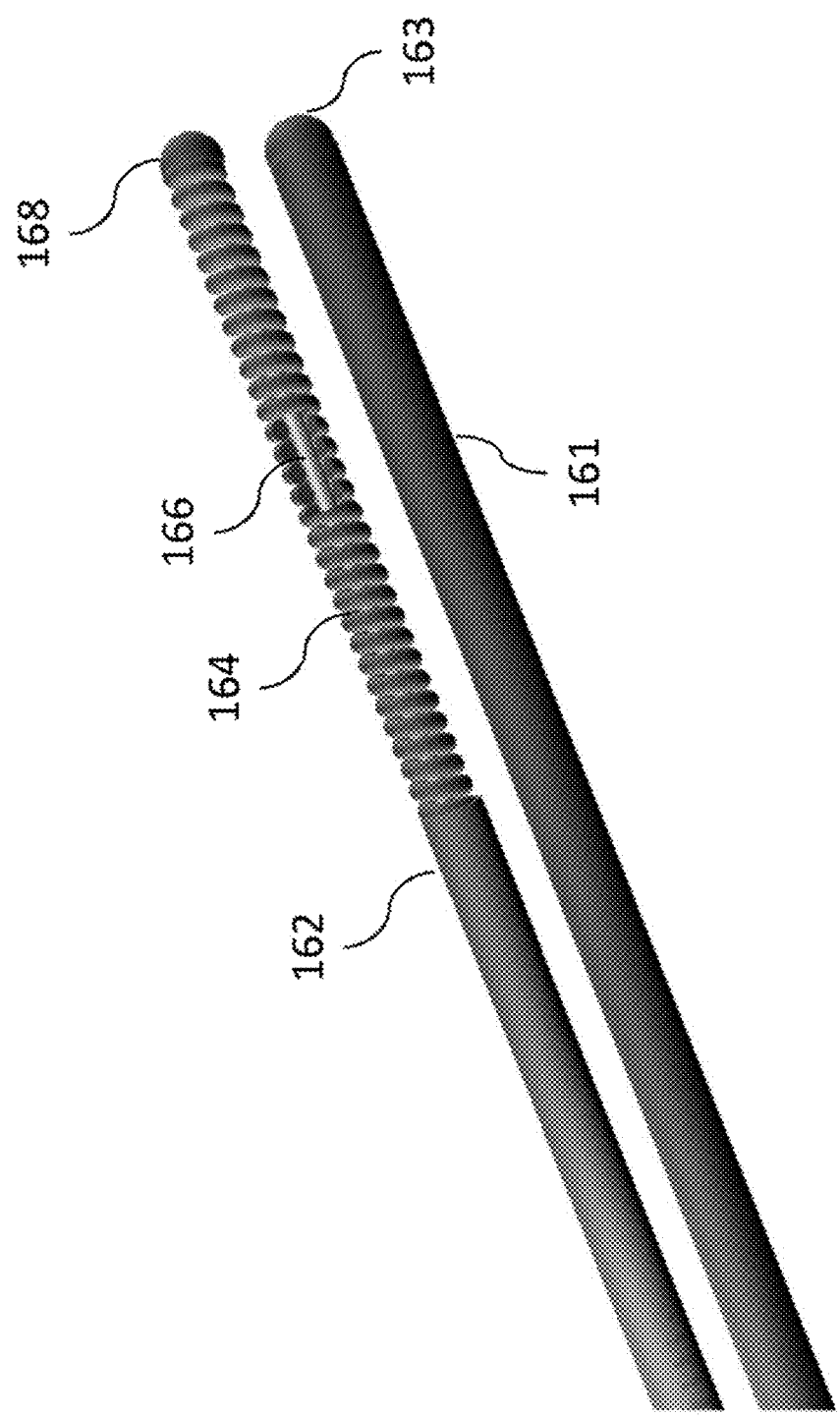
FIG. 1e illustrates an exemplary guide wire with a blunt tip and an exemplary guide wire with a blunt tip.

FIG. 1e illustrates an exemplary guide wire 161 having a blunt tip 163 and an exemplary guide wire 162 having a blunt tip 168. The guide wire 162 can include a coiled section 164, where a cut-out portion illustrates a core wire 166. The core wire 166 can be used for activation of the guide wire.

Figure 1F:
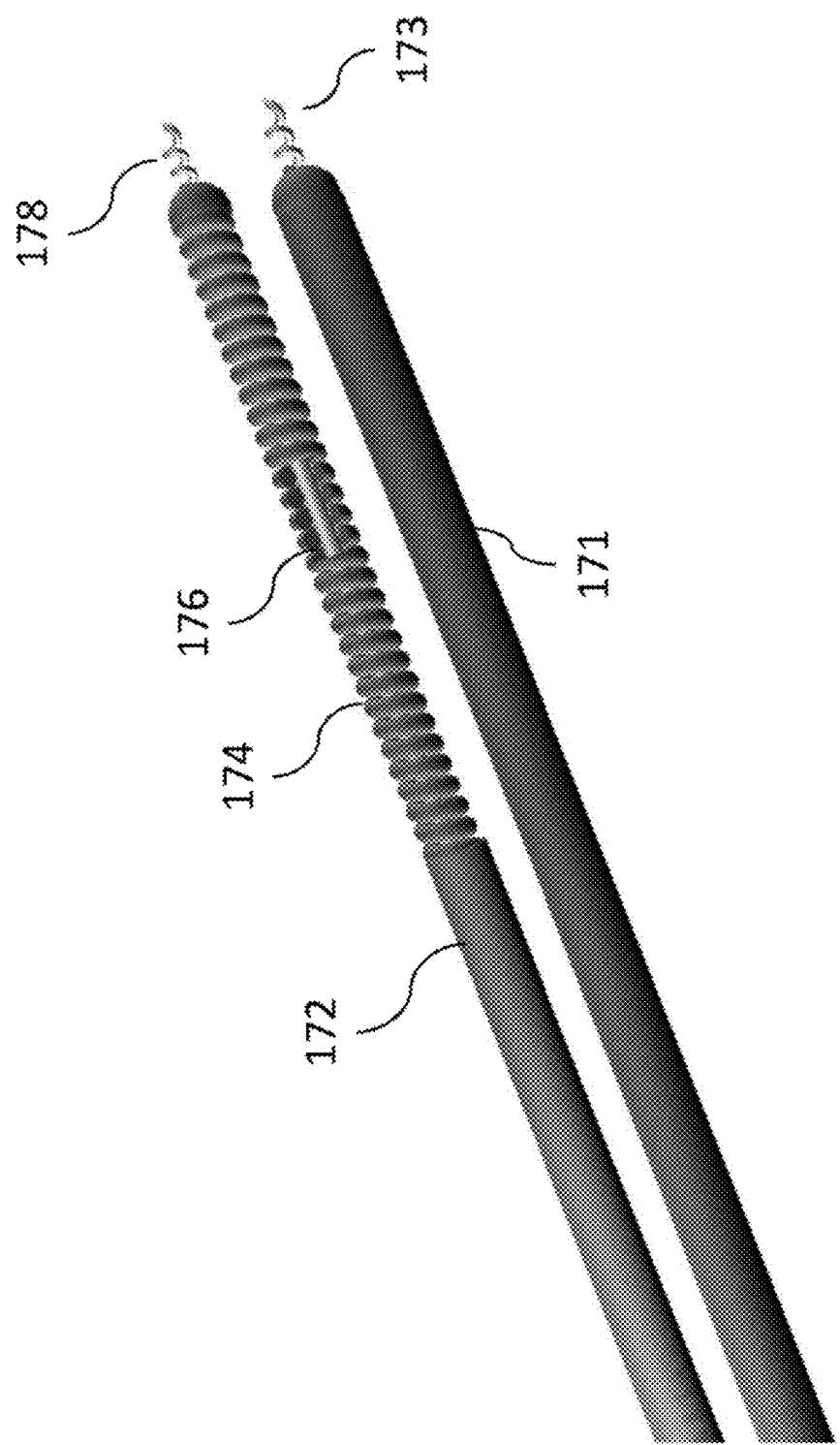
FIG. 1f illustrates another exemplary guide wire with a screw tip and an exemplary guide wire with a screw tip.

FIG. 1f illustrates another exemplary guide wire 171 having a screw tip 173 and an exemplary guide wire 172 having a screw tip 178. In some implementations, the guide wire 172 can be configured to conform to a screw tip once the guide wire is unsheathed from a catheter. Similar to FIG. 1e, the guide wire 172 can include a coiled section 174. The cut-out portion shown in FIG. 1f illustrates a core wire 176 that can be used for activation of the guide wire.

In some implementations, a tool can be made available to remotely adjust a distance between the core wire end and the guide wire coil. In some implementations, the guide wire coil and/or segmented tube can be placed over the entire length of the guide wire. Thus, the shape of the guide wire's anchoring section can be changed remotely, as discussed above, using the slidable core wire positioned inside the guide wire's interior. This can, for example, be used to determine an amount of enlargement of a basket (or any other anchoring configuration mechanism) that may be incorporated into the anchoring section of the guide wire. Similarly, a flat, square and/or otherwise shape of the catchable section of the core wire can allow for applying force (e.g., torsion, traction, etc.) to the core wire, which in turn, can be transmitted to the anchoring section and allow for changing of the shape in situ. Further, a guide wire with a conical and/or spiral anchoring configuration/mechanism of the anchoring section after unsheathing can be remotely rotated (e.g., screwed) into position using a rotation tool (e.g., which can be any known torque device). The rotation can be performed up to a certain predetermined torque value in order to limit potential damage to tissue surrounding in the anchoring section. In alternate implementations, the hollow interior of the guide wire can allow activation of the anchoring section using at least one of the following: a fluid substance (e.g., saline, contrast medium, etc.), a gaseous substance (e.g., air, $CO_2$, Helium, etc.), pressurizing means (e.g., a compressor, etc.) and/or any other means, and/or any combination thereof. Moreover, a spring mechanism can be built into the anchoring section and can be activated by a current (e.g., galvanic corrosion), a spindle, a motor, etc. These devices can be attachable to and/or detachable from the guide wire steering section. The attachment/detachment can be performed once the device to be implanted is loaded onto the guide wire, but not yet in the implantation section of the guide wire. The transfer of the device can be performed using traction of the guide wire, which holds the guide wire at the anchoring location. The traction can be adjusted manually and/or using specific device allowing for measurement and/or servo-tension-optimization.

In addition to friction fixation, the current subject matter can also allow for fixation of the form of the guide wire portions. In some implementations, the shape change in-situ can conform partially and/or entirely to the shape of the anchoring location of the guide wire and thus, hold the guide wire in place while traction is applied. Once the fixation of the shape is no longer required, the original shape of the guide wire can be re-established, thereby allowing retraction through a catheter. This can be achieved using a reverse action of the mechanism used for shape change, re-sheathing etc. (as shown, for example, in FIG. 5).

FIG. 1a illustrates a conventional guide wire 102, and an exemplary guide wire 104, according to some implementations of the current subject matter. The conventional straight guide wire 102 is currently and routinely used in various procedures.

The current subject matter's guide wire 104 can include a navigation section or tip 106, an anchoring section 108, a device implantation section 110, a device transfer section 112, and a steering section 114. The tip 106 can be located at a distal end of the guide wire 104 and can be inserted into an access opening and/or navigated toward a target location and/or an anchoring location (i.e., a location where anchoring section can be actuated into an expanded state). The steering section 114 can be located at a proximate end of the guide wire 104 and can be positioned, at least partially, outside the access opening.

As shown in FIG. 1a, the anchoring section 108 can include an anchoring mechanism. FIG. 1a illustrates the anchoring mechanism as a series of co-axial loops. The loops can be designed to provide friction once positioned in an anchoring location and/or the target location. The anchoring location can be any vessel (e.g., aorta, artery, vein, etc.), organ, cavity, opening, etc. in a body of the patient. The anchoring/target location can have dimensions that can be less than the dimension of the co-axial loops (e.g., diameter of the anchoring location can be less than the diameter of the co-axial loops). The loops can have a uniform diameter throughout. Alternatively, a diameter of one loop can be different from another loop's diameter. Further, there can be any number of loops in the anchoring section 108. As stated above, the anchoring section 108 is not limited to the co-axial loops shown in FIG. 1a. In some implementations, the anchoring section 108 can include coils, angles, Z-shapes or zig-zag shapes, etc. The anchoring section 108 can have a two-dimensional and/or a three-dimensional structure and/or any combinations thereof. The anchoring section 108 can be active and/or passive, permanent and/or temporary, etc., and/or any combination thereof. The anchoring section 108 can also have various configurations, e.g., baskets, balloons, pyramids, screws, etc., and/or any combination thereof. Further, one or more portions of the anchoring section 108 can include various surface treatments that can increase friction, including but not limited to, specific coatings (e.g., chemical, mechanical, etc. coatings), knobs, ribs, magnets, spikes, hooks, secondary coils etc., and/or any combination thereof. The surface treatments can be entirely, partially and/or otherwise be sheathed and re-sheathed during implantation procedure. In some implementations, one or more parts of the anchoring section 108 can have varying degrees of stiffness (e.g., one part can be stiffer (or more flexible) than another part). The stiffness of each part and/or the entire anchoring section 108 can be determined as a function of the guide wire 104's configuration and/or use during insertion and/or during traction as well as planned traction forces, expected target site specification, re-sheathing and/or removal forces for re-sheathing/removal of the guide wire, and/or any combination thereof.

FIG. 1b illustrates further details of the guide wire system 104 shown in FIG. 1a. FIG. 1b illustrates angles α and β that can be formed between the device implantation section 110 and the anchoring section 108. The angles α and β can be formed once the anchoring section is actuated into an expanded stated. One or more of such angles can be formed and can improve anchoring of the guide wire at the anchoring location, re-sheathing and/or removal of the guide wire, etc. For example, narrower or smaller angles α and β can cause an increase in forces that may be required to overcome friction created by the anchoring section when the guide wire is anchored at the anchoring location. Further, narrower/smaller angles α and β can make it more difficult to re-sheath the coiled guide wire with a straight catheter for the purposes of removal. In contrast, wider or larger angles α and β can reduce friction that may be created by the anchoring section while at the same time making device implantation easier as well as re-sheathing/removal of the guide wire. The angles α and β can be any angles in the range of 0° to 360°. In some implementations, the anchoring can depend on angles α and/or β and/or size (e.g., radius, etc.) of the curvature that the anchoring section may form. For example, for removal purposes, a narrower angle (e.g., hook) may be more difficult to remove, but can be compensated using a larger radius section.

FIG. 1c illustrates cross-sections of the exemplary guide wire 122 having a hollow interior that can allow a slidable insertion of a core wire 120. Alternatively, instead of the core wire 120, the hollow interior of the guide wire 122 can be used for delivery of liquids, gases, current, etc., such as, for the purposes of actuating and/or de-activating the anchoring mechanism in the anchoring section of the guide wire.

Figure 2:
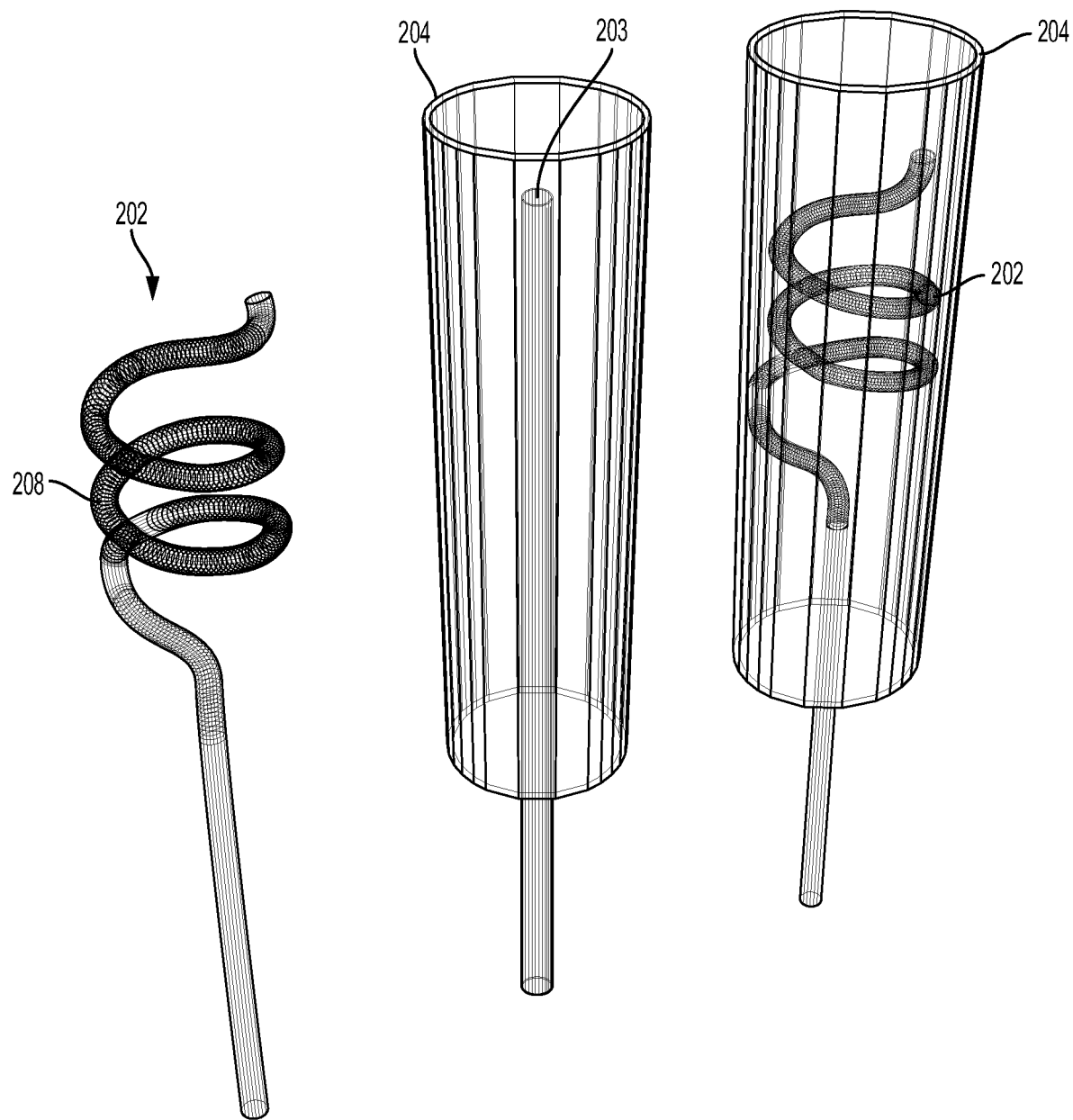
FIG. 2 illustrates an exemplary guide wire, according to some implementations of the current subject matter.

FIG. 2 illustrates an exemplary guide wire 202, according to some implementations of the current subject matter. The guide wire 202 can be similar to the guide 104 shown in FIG. 1a. The guide wire 202 can include a co-axial coil 208 as part of its anchoring section. The co-axial coil 208 can provide friction and can prevent movement of the guide wire 202 once the guide wire 202 has been inserted and/or anchored at a target location, e.g., a vessel (and/or any vessel, organ, cavity, opening, etc.) 204, as shown in FIG. 2. In some implementations, the guide wire 202 can be inserted using a straight catheter and/or can be stretched to within a catheter to configuration 203 (as shown by the middle portion of FIG. 2). Prior to insertion, the guide wire 202 can be formed into a desired configuration (e.g., zig-zags, coils, etc.) using shape memory materials, tension, etc., then a straightening catheter and/or any other device, which can straighten the guide wire (e.g., temporarily) into configuration 203, can be used to allow insertion of the guide wire into the anchoring location. For example, the straightening can be accomplished using a pulling and/or pushing force and/or any other tensioning force that can be exerted using the core wire (not shown in FIG. 2) and/or any other means (e.g., liquids, gases, pressurizing means, current, etc.). The force can be applied to the guide wire outside of the access opening through which the guide wire 204 has been inserted. Further, in an eccentric configuration of the guide wire body with reference to the guide wire anchoring coil, the guide wire can be centered using rotation with respect to its device's carrying section. Once the guide wire (and the catheter) is placed into the anchoring location, the catheter can be removed causing the guide wire to assume its original shape (e.g., zig-zags, coils, etc.). As such, the guide wire, upon assuming its original shape, can friction-fit, form-fit and/or be actively and/or passively fixed at the anchoring location.

Alternatively, the guide wire can self-expand once the guide wire is positioned at the anchoring location. In this case, the guide wire can have a self-expanding design, whereby the guide wire anchoring section (and/or any other sections) can have a predetermined expanded configuration (which can be manufactured from, for example, memory shape materials, thermo-sensitive nitinol, non-thermo-sensitive nitinol, stainless steel, polyester, etc., and/or any combination thereof). Prior to delivery of the guide wire to the anchoring location, the anchoring section of the guide can be stretched using a straightening catheter (and/or any other device). Upon insertion of the guide wire (which can be sheathed) to the anchoring location, the catheter can be removed or pulled back, thereby unsheathing the guide wire's anchoring section. Once unsheathed, the anchoring section can automatically expand into an expanded state (or a state held by the anchoring section prior to stretching) to create a friction fit and/or form fit with the interior of the anchoring location.

Referring back to FIG. 2, once the coils 208 of the guide wire 202 are formed, the coils 208 can be pushed against inner walls of the anchoring location (e.g., a vessel, organ, cavity, opening, etc.), thereby creating a "friction fit" structure that can prevent guide wire from moving in and out of the anchoring location. In some implementations, the size (e.g., a diameter) of the co-axial coil 208 can be slightly larger than the inner diameter of the anchoring location. In some implementations, dimension(s) of the expanded anchoring section can be determined by assessing the anchoring location, such as, by using imaging, ultrasound, CAT scans, x-rays, etc. before and/or during the procedure. In some implementations, the size of the anchoring section can also be adjusted in situ to ensure that an appropriate anchoring is created without damaging the anchoring location. The angles α and β (as shown in FIG. 1b) can also be adjusted to ensure proper anchoring. This can be accomplished using the core wire and/or other means discussed above.

In some implementations, to insert a device (e.g., a catheter, a probe, a cannula, and/or any other device, and/or any combination of devices), the guide wire 202 can be tensioned, thereby straightening at least one part of the guide wire 202.

In some implementations, to insert (or position or implant, etc.) a device (e.g., a catheter, a probe, a cannula, etc.), a target location (e.g., a target vessel) can be selected and approached using a guide wire and a catheter using an introducer sheath. One or more sections of the guide wire, such as the one shown in FIGS. 1a-2, can be configured to change shape in-situ (i.e., at the anchoring location). The guide wire can be advanced to the target location and then can be further advanced for positioning beyond the target location, i.e., to the anchoring location. This can allow maintaining of a path or an axis for insertion of the device over the guide wire at all times. In some implementations, the guide wire can be advanced using a catheter. At the anchoring location, the guide wire, and in particular, its anchoring section, can be configured to change shape (e.g., form coils, rings, baskets, etc.) for the purposes of anchoring the guide wire at the anchoring location. The target location or implantation location can be the location where the device (e.g., a catheter, a probe, a cannula, etc.) can be implanted. The target/implantation location can coincide with the implantation section of the guide wire.

Once the guide wire is positioned at the anchoring location, a catheter can be used to tension (e.g., contract, expand, etc.) respectively release the guide wire. The tension can cause a change in the shape of the anchoring section of the guide wire. The guide wire's anchoring section can expand to be slightly larger than the inner dimension (e.g., a diameter) of and up to the inner walls of the anchoring location. This expansion can create an anchoring and/or friction fit and/or form fit effect that can retain the guide wire at the anchoring location.

In some implementations, the anchoring of the guide wire can be checked by applying a pulling force on the guide wire to determine whether or not the guide wire is moving. Alternatively, imaging means (e.g., ultrasound, CAT scan, x-ray, etc.) can be used to ensure proper positioning and/or anchoring of the guide wire. If the anchoring is inadequate, the guide wire can be re-sheathed by pulling it back into the catheter, re-positioned and the anchoring process repeated. This procedure can be repeated as required. Once adequate anchoring is determined, the catheter that can be used for anchoring the guide wire can be removed. Then, the device can be transferred over the anchored guide wire to the target location. Further, by applying tension to the guide wire, any kinks in the guide wire can be removed/straightened. As soon as the implantation procedure is completed, the guide wire can be re-sheathed using the device's carrying catheter and/or another catheter and removed either through, or together with the catheter.

FIGS. 10a-13d illustrate exemplary, non-limiting, experimental traction curves associated with positioning an exemplary guide wire, according to some implementations of the current subject matter. FIGS. 10a-13d illustrate forces that are required for pulling back a stiff 0.035" guide wire having a coiled friction portion through various tubes. In some implementations, a device carrying catheter can be used for withdrawal/removal purposes.

Figure 10A:
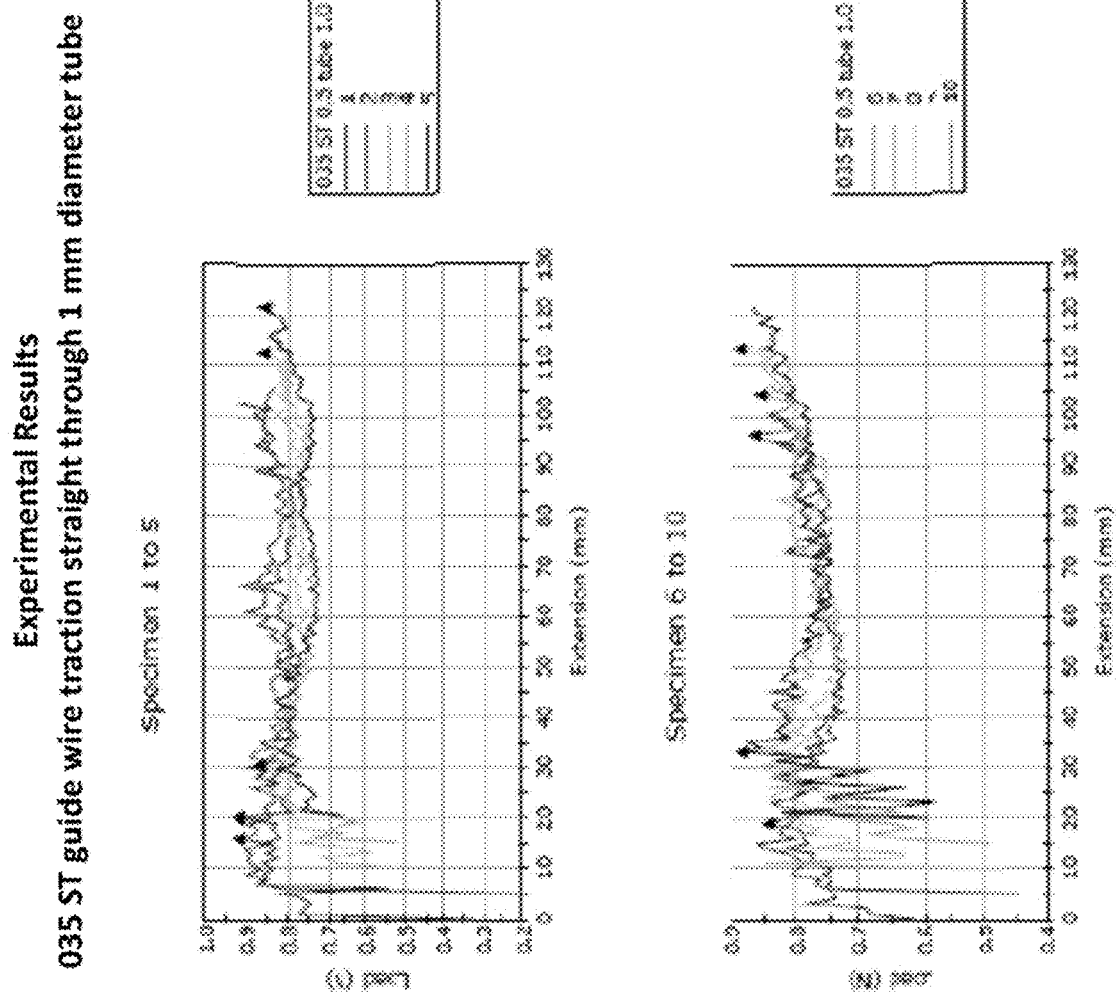
FIGS. 10a-b illustrate exemplary experimental results, according to some implementations of the current subject matter.
Figure 10B:
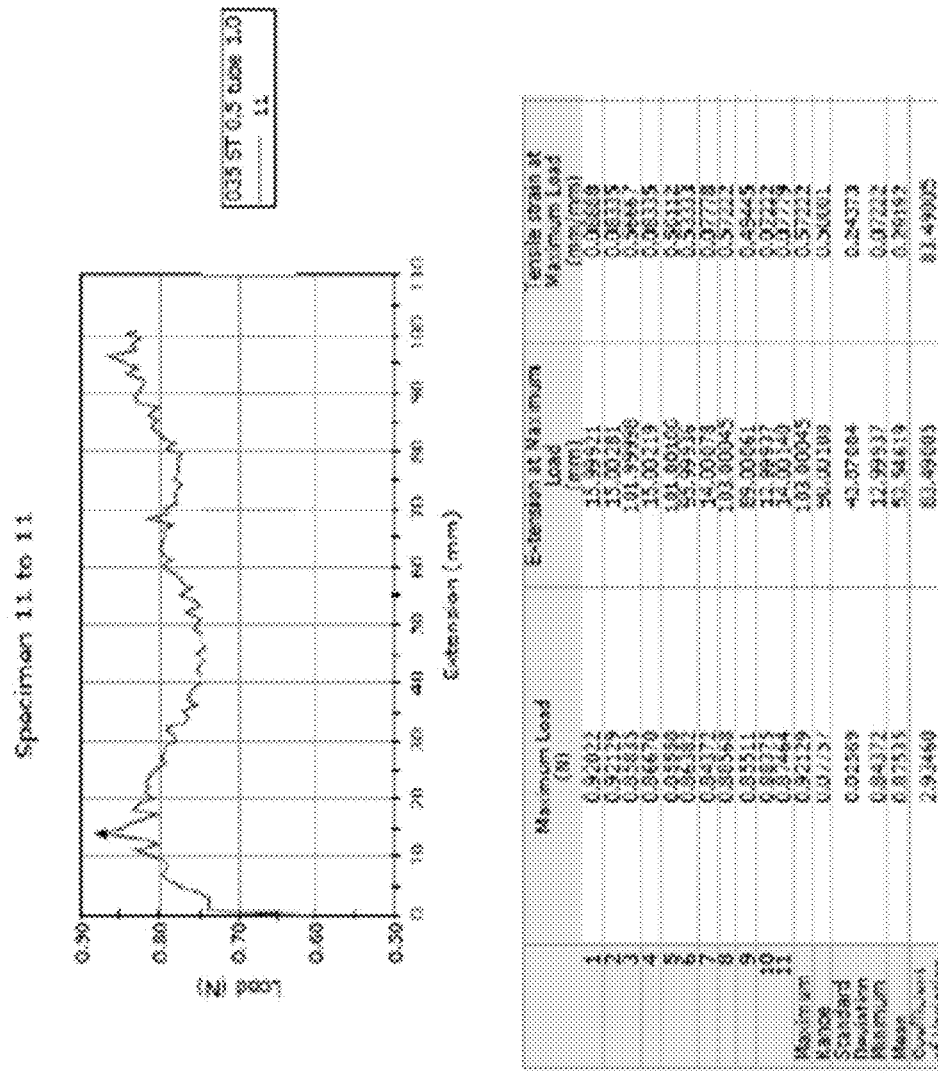

FIGS. 10a-b illustrate exemplary experimental traction data for 11 samples/specimens. The experiments shown in FIGS. 10a-13b were conducted using same guide wire type(s) (i.e., coated, stainless steel and nitinol combination) but having different configurations. Referring back to FIGS. 10a-b, the 0.035" ultra-stiff coiled guide wire was positioned through a tube having 1 mm diameter. In this case, a maximum mean traction load allowed by the guide wire is approximately 0.87±0.02 Newton ("N") and the approximate range is 0.84 N-0.92 N. At maximum load, a mean extension of the guide wire is approximately 52.54±42.87 mm and the approximate extension range is 12.99 mm-103.00 mm. A tensile strain at maximum load is approximately 0.29±0.24 mm/mm and the approximate extension range is 0.07 mm/mm-0.57 mm/mm.

Figure 11A:
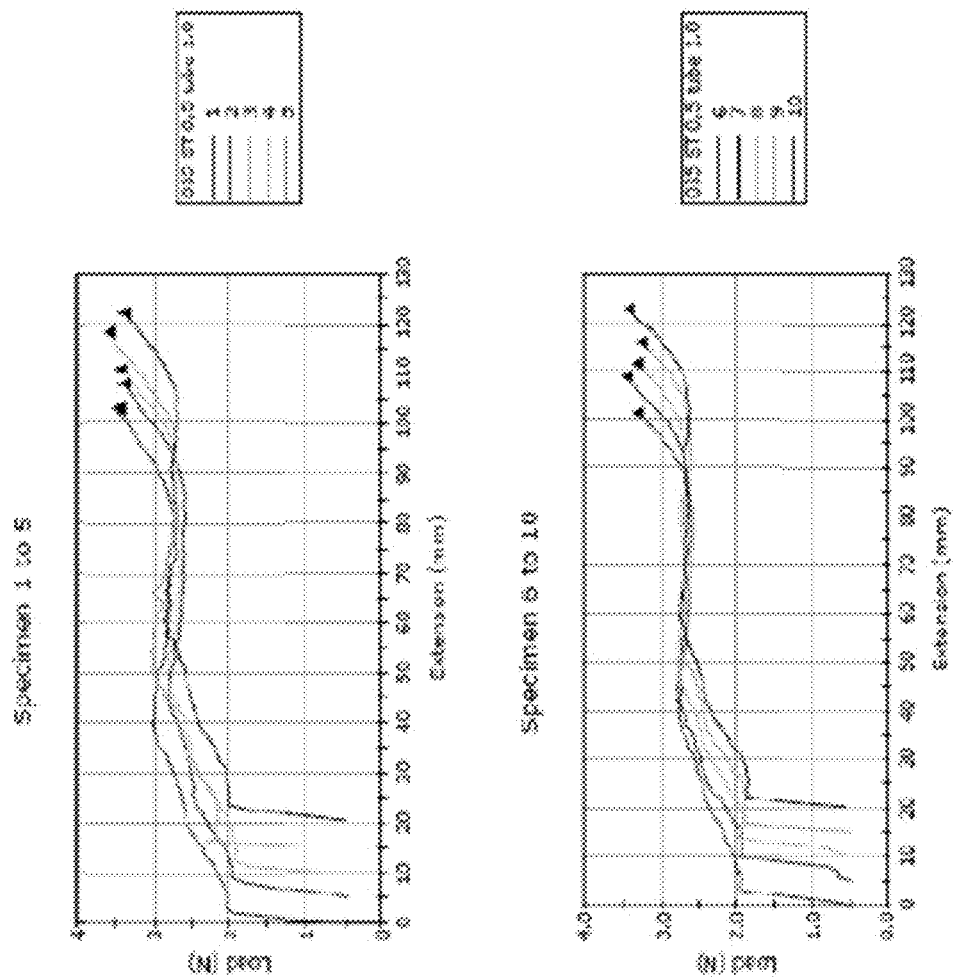
FIGS. 11a-b illustrate exemplary experimental results, according to some implementations of the current subject matter.
Figure 11B:
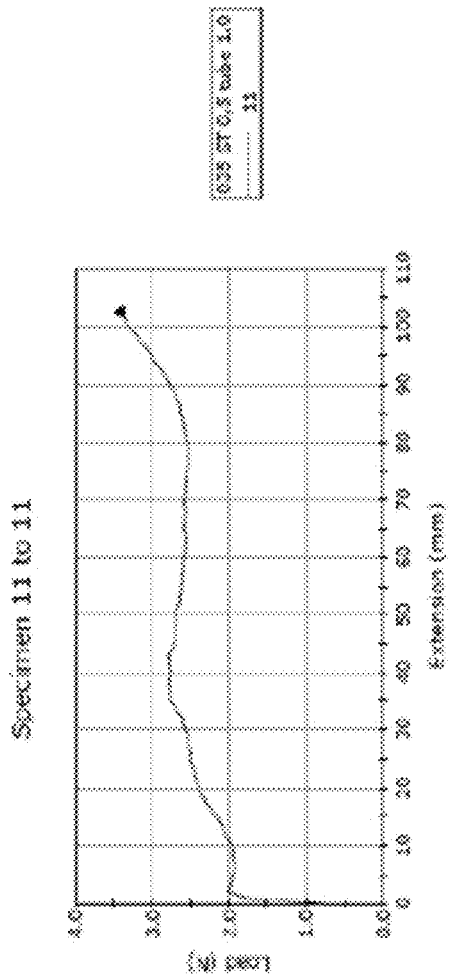

FIGS. 11a-b illustrate exemplary experimental traction data for 11 samples/specimens when the 0.035" guide wire having loose loops (having a thread pitch of 20 mm) with radius 10 mm is positioned through a tube having 9 mm diameter. Here, a maximum mean traction load allowed by the guide wire is approximately 3.40±0.09 Newton ("N") and the approximate range is 3.24 N-3.58 N. At maximum load, a mean extension of the guide wire is approximately 101.79±1.02 mm and the approximate extension range is 100.23 mm-103.36 mm. A tensile strain at maximum load is approximately 0.56±0.005 mm/mm and the approximate extension range is 0.55 mm/mm-0.57 mm/mm.

Figure 12A:
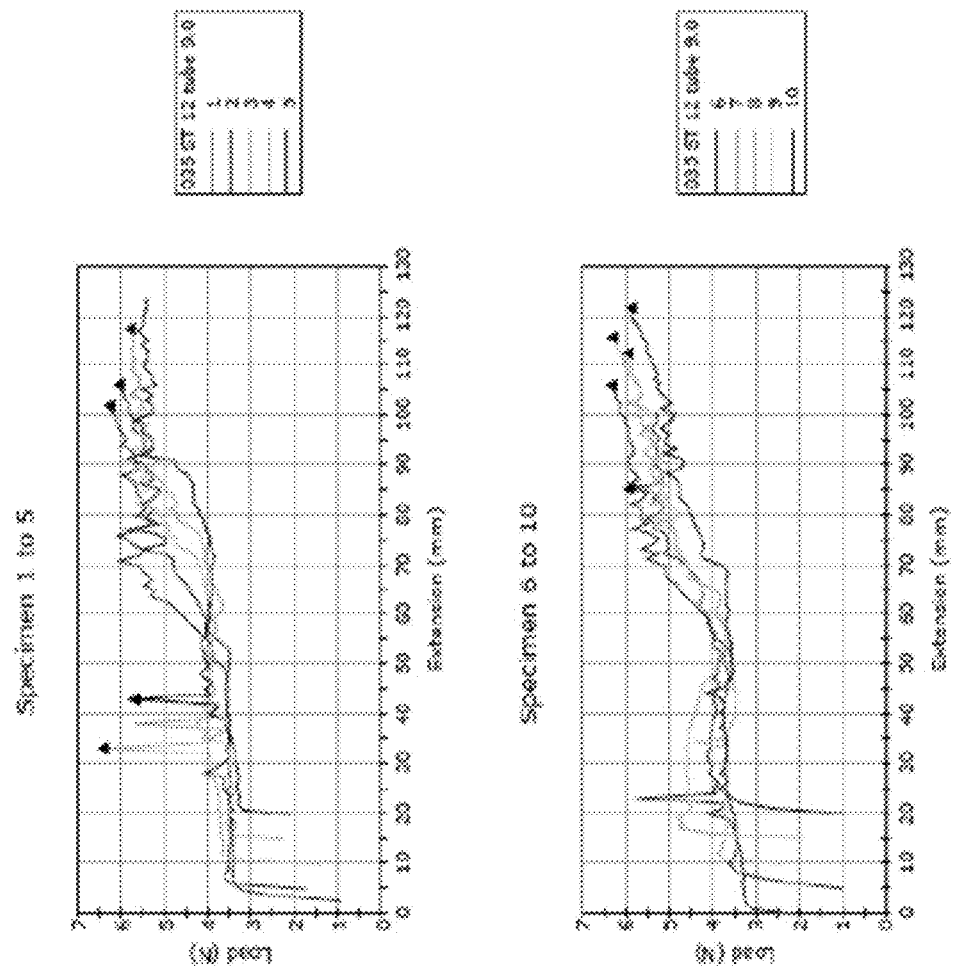
FIGS. 12a-b illustrate exemplary experimental results, according to some implementations of the current subject matter.
Figure 12B:
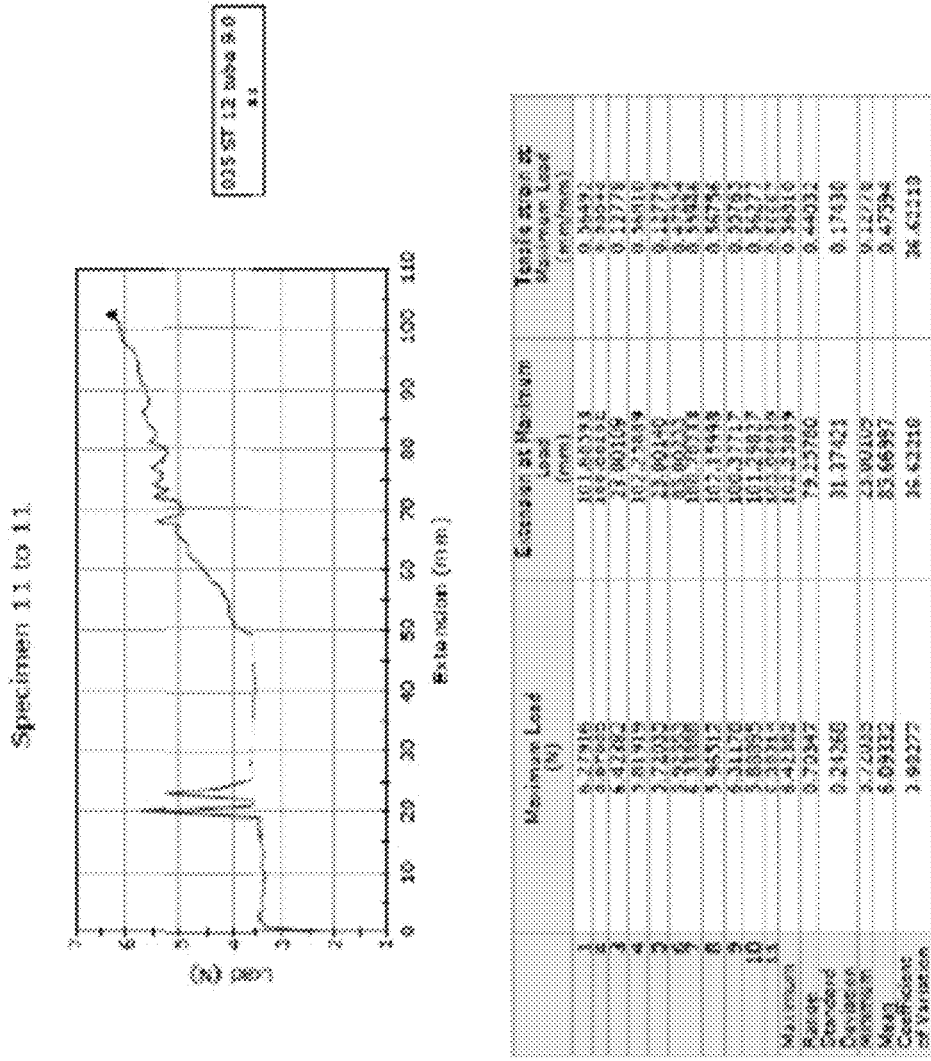

FIGS. 12a-b illustrate exemplary experimental traction data for 11 samples/specimens when the 0.035" guide wire having loose loops (having a thread pitch of 20 mm) with radius 12 mm is positioned through a tube having 9 mm diameter. Here, a maximum mean traction load allowed by the guide wire is approximately 6.09±0.24 Newton ("N") and the approximate range is 5.72 N-6.42 N. At maximum load, a mean extension of the guide wire is approximately 85.66±31.37 mm and the approximate extension range is 23.00 mm-102.25 mm. A tensile strain at maximum load is approximately 0.47±0.17 mm/mm and the approximate extension range is 0.12 mm/mm-0.56 mm/mm.

Figure 13A:
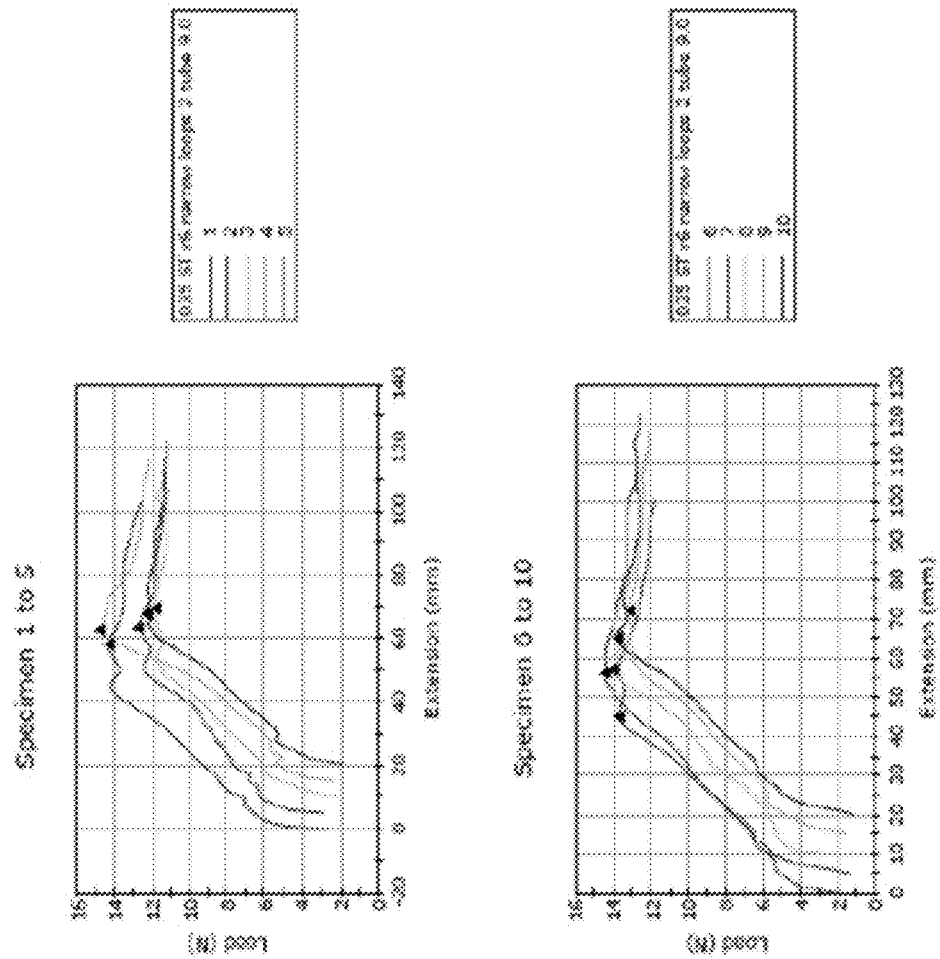
FIGS. 13a-b illustrate exemplary experimental results, according to some implementations of the current subject matter.
Figure 13B:
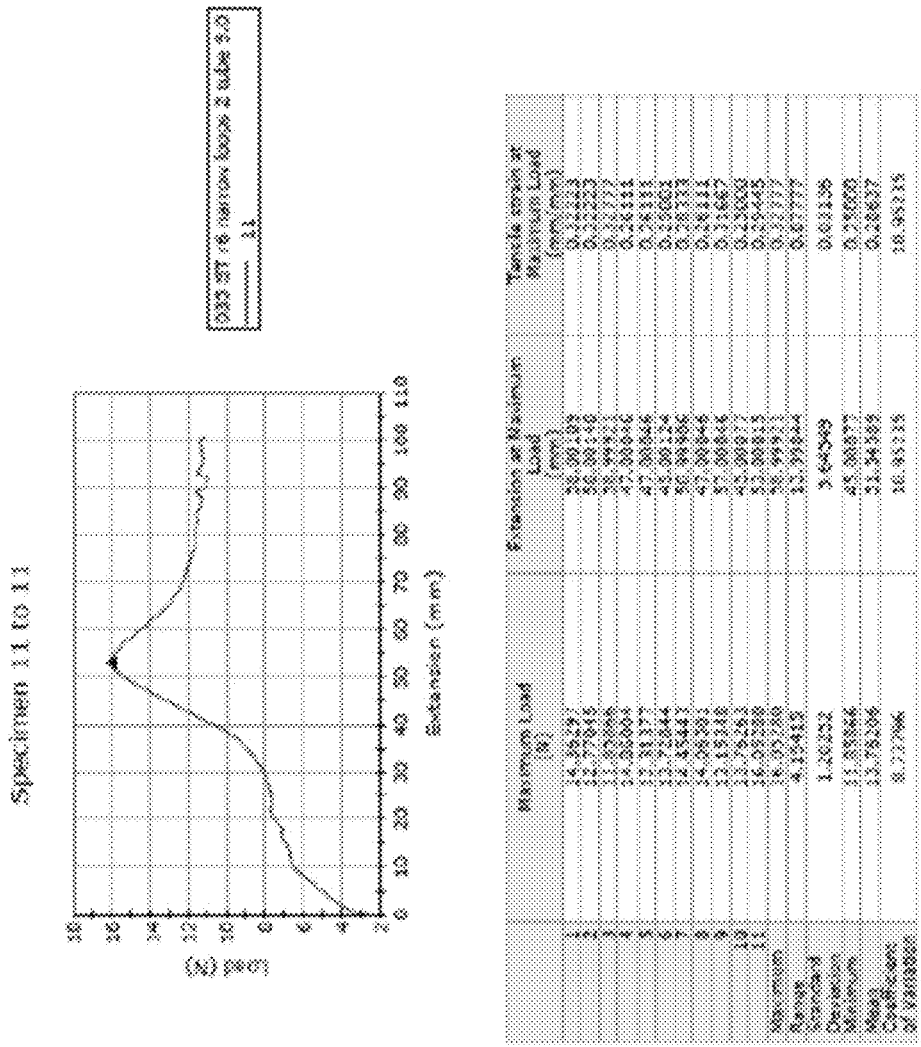

FIGS. 13a-b illustrate exemplary experimental traction data for 11 samples/specimens when the 0.035" guide wire having two narrow loops (having a thread pitch of 10 mm), each having a radius of 6 mm, is positioned through a tube having 9 mm diameter. In this case, a maximum mean traction load allowed by the guide wire is approximately 13.76±1.20 Newton ("N") and the approximate range is 11.86 N-16.05 N. At maximum load, a mean extension of the guide wire is approximately 51.54±5.64 mm and the approximate extension range is 45.00 mm-58.99 mm. A tensile strain at maximum load is approximately 0.28±0.03 mm/mm and the approximate extension range is 0.25 mm/mm-0.32 mm/mm.

Figure 3:
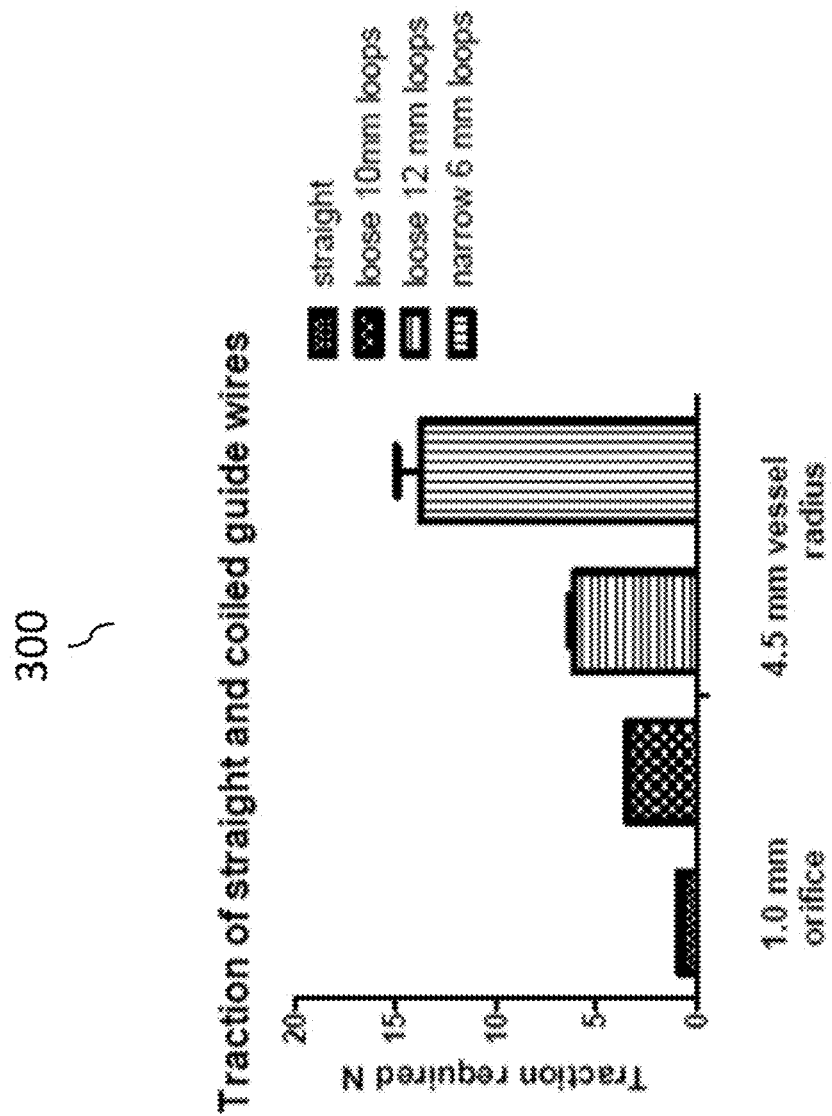
FIG. 3 is an exemplary plot illustrating traction of straight and coiled guide wires, according to some implementations of the current subject matter.

FIG. 3 is a plot 300 illustrating exemplary traction forces that may be required to pull straight guide wires using a 1 mm orifice (which can correspond to the value for the orifice as used in existing procedures) and coiled guide wires using a 4.5 mm vessel radius. The plot 300 demonstrates that pulling back a 0.035" guide wire through a 1.0 mm orifice can require approximately 1.0 N. The coiled and kinked guide wires can require additional force to pull back through a narrow orifice, e.g., a catheter. The guide wires can be coiled to increase force that can be required for a pull-back (e.g., more than one order of magnitude despite a much larger vessel substitute). Further, the shape of the friction portion of the guide wire (e.g., coil, loops, etc.) can affect the amount of force that may be required. For example, increase in the number of coils and/or inclusion of special configurations, rough surface treatments, small spikes, etc. can further increase the amount of force that may be required. These additional features can be included in the guide wire provided that the guide wire can be re-sheathed with a catheter for removal, once the device implantation procedure is completed. In some exemplary implementations, the coils can have at least one of the following shapes: loop(s), spiral(s), coil(s), curl(s), zig-zag(s) (e.g., arranged in a cylindrical configuration), and/or any other shapes, and/or any combination thereof. In some implementations, the coiled guide wire can be pulled back through a stiff catheter, and thus, removed without sequelae after the device implantation procedure is completed.

In some implementations, geometries of the anchoring section of the guide wire that provide friction at the anchoring location can be included in guide wires that can contain multiple filaments including a core wire and one or more coils, etc. The core wire can be used to activate a basket, a diabolo, a cylinder, a cone, an inverted cone, a pyramid, and/or any other shapes, and/or any combinations thereof. In some implementations, multiple baskets can be stacked in an accordion-like fashion, and can be expanded at the anchoring location. Such multiple baskets can be used to provide additional friction at the anchoring location, thereby, allowing straightening of the guide wire to improve implantation of a device (e.g., a catheter, a probe, a cannula, etc.).

Figure 4:
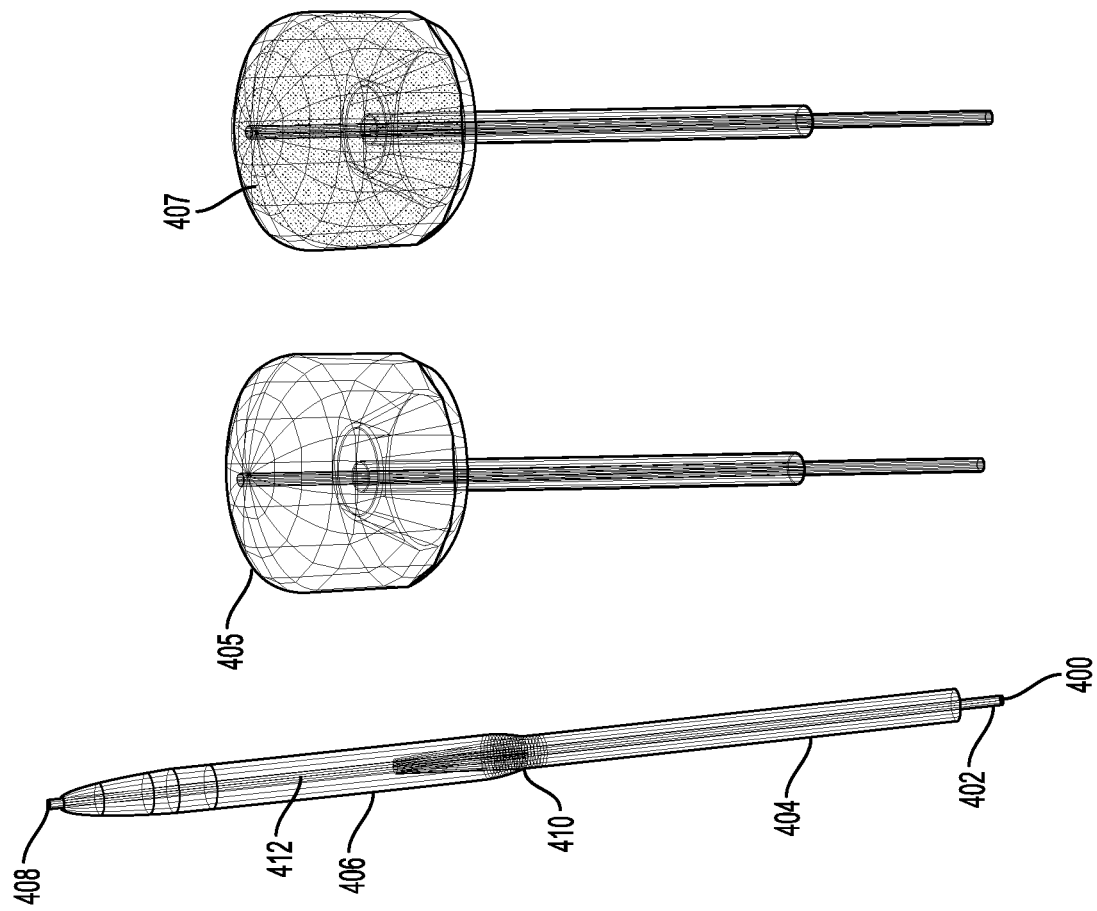
FIG. 4 illustrates another exemplary guide wire, according to some implementations of the current subject matter.

FIG. 4 illustrates an exemplary guide wire system 400, according to some implementations of the current subject matter. The guide wire system 400 can include a core wire 402, a guide wire 404, a basket 406, and a tip 408. The guide wire 404 can include a hollow interior that can allow insertion of the core wire 402. The tip 408 can correspond to the distal end of the core wire 402. The tip 408 can be coupled to a top of the basket 406. The bottom of the basket 408 can be coupled to the distal end 410 of the guide wire 404. The guide wire system 400 can be inserted to a target location, where at least a part of a portion 412 of the system 400 can be advanced to an anchoring location, which can be past the target location. The portion 412 can be located between the tip 408 and the distal end 410 of the guide wire 404. Once at the anchoring location, the core wire 402 can be pulled, thereby sliding inside the guide wire 404. This can force the top and the bottom of the basket 406 to advance toward each other and expand the basket 406 into an expanded state 405.

The expanded state 405 of the basket 406 can expand toward and/or push against the interior walls of the anchoring location. This can create a friction fit between the basket and the interior of the anchoring location, thereby preventing movement of the guide wire 404 during device implantation procedures. Alternatively, a form fit can also be achieved through appropriate basket design. In some implementations, the expanded state 405 can have a size (e.g., diameter) that can be slightly larger than the dimension (e.g., diameter) of the anchoring location. In some implementations, the expanded state 405 can have a size that is larger than the dimension of the target location (but not necessarily the anchoring location).

In some implementations, the system 400 can include a locking mechanism (not shown in FIG. 4) that can lock the basket 406 in the expanded state 405. This can ensure that the basket 406 does not collapse during device implantation procedure. The locking mechanism can be located in the basket 406 (e.g., hooks, pins, etc.), and/or can be located externally to the system 400. The locking mechanism can be released thereby releasing the basket 406 from a locked state, thereby causing a collapse of the basket 406 into a contracted state as shown in FIG. 4 on the left side. In some implementations, the core wire 402 can be pushed toward the tip 408 to return the basket 406 into a contracted state. In some implementations, the basket 406 can be manufactured from shape memory materials, e.g., Nitinol, etc. This can allow expansion and contraction of the basket 406 to a predetermined size (e.g., diameter, width, length, etc.). Further, expansion and contraction of the basket 406 can be performed using liquids, gases, electric current, etc. and/or any other means and/or any combination thereof.

In some implementation, a balloon 407 can be used in conjunction with the basket 406 and/or by itself. The balloon 407 can be used to increase friction during the device implantation procedure.

In some implementations, the tip 408 can be configured to have a small sharp spiral as shown in FIG. 1f. This can allow rotating (or screwing) the tip 408 at a suitable place in order to further anchor the system 400 during a device implantation. Alternatively, the guide wire tip can form a screw upon activation and/or unsheathing.

Figure 5:
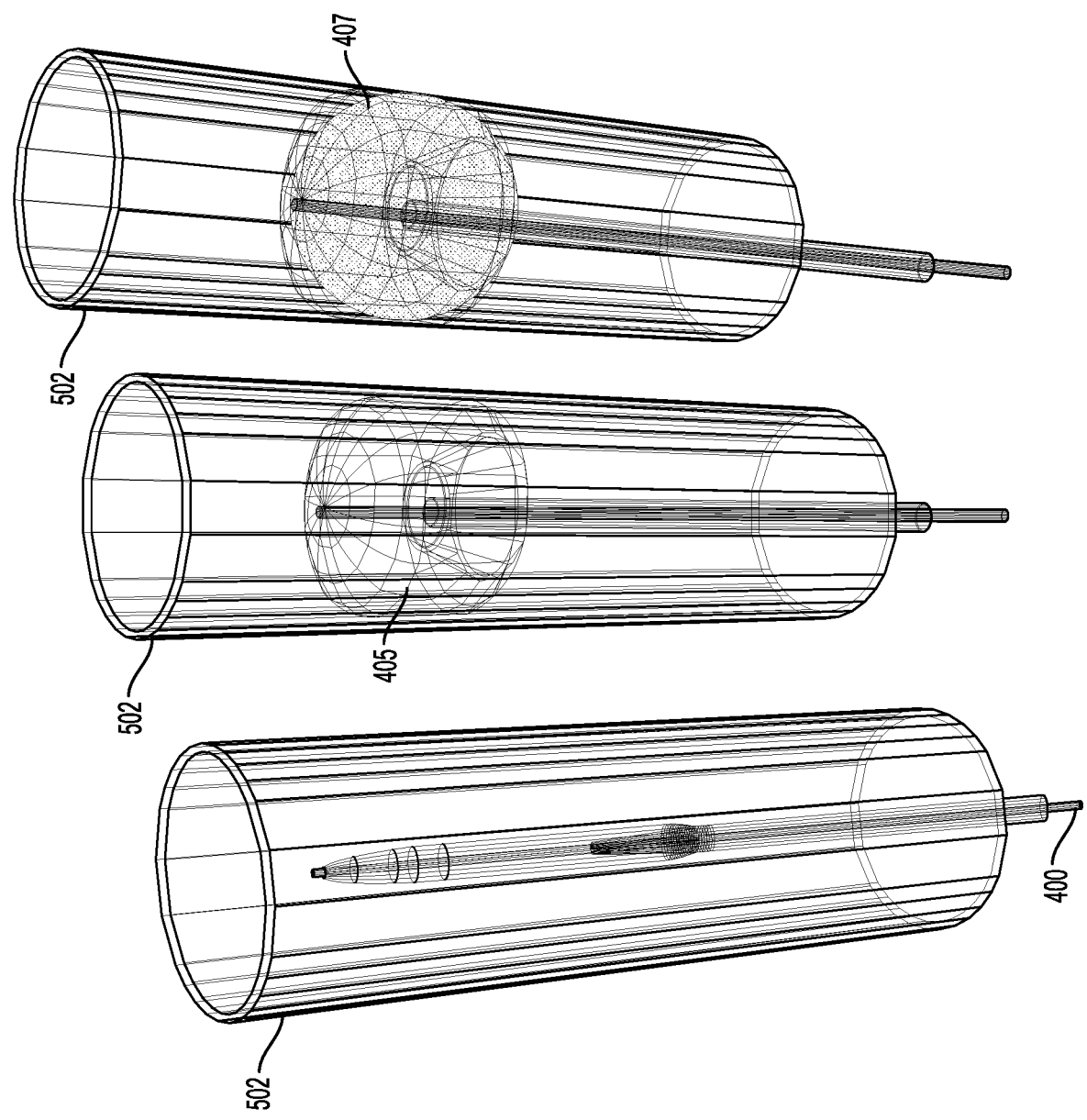
FIG. 5 illustrates another exemplary guide wire, according to some implementations of the current subject matter.

FIG. 5 illustrates an exemplary guide wire system 400 shown in FIG. 4 being positioned in an anchoring location (e.g., vessel, organ, cavity, opening, etc.) 502. Initially, the system 400 having its basket in a contracted and/or a sheathed state (as shown by the diagram on the left side) is advanced into the anchoring location 502. Positioning of the system 400 can be confirmed using various means, including, but not limited to, x-rays, angiograms, CAT scans, etc. Once in position, the basket 406 can be activated and/or unsheathed and placed into an expanded state 405. In the expanded state 405, the basket 406 can be expanded up to the interior walls of the anchoring location 502. The expanded state 405 of the basket 406 can have larger dimensions than the interior dimensions of the anchoring location 502. This can create a friction fit positioning, which can prevent the system 400 from moving and/or dislodgement during device implantation procedure. To further increase friction, a balloon 407 (as shown by the diagram on the right) can be configured to be included with the basket 406. In some implementations, the current subject matter can include various friction-generating geometries in addition to the basket 406, which can include, but are not limited to, a ball, an ovoid, a diabolo-shape configuration, a cylinder, a cone, an inverted cone, a cup (e.g., a cup that can be used with a vacuum, i.e., a suction cup), a pyramid, an accordion, and/or any other shapes, and/or any combination thereof.

Figure 6:
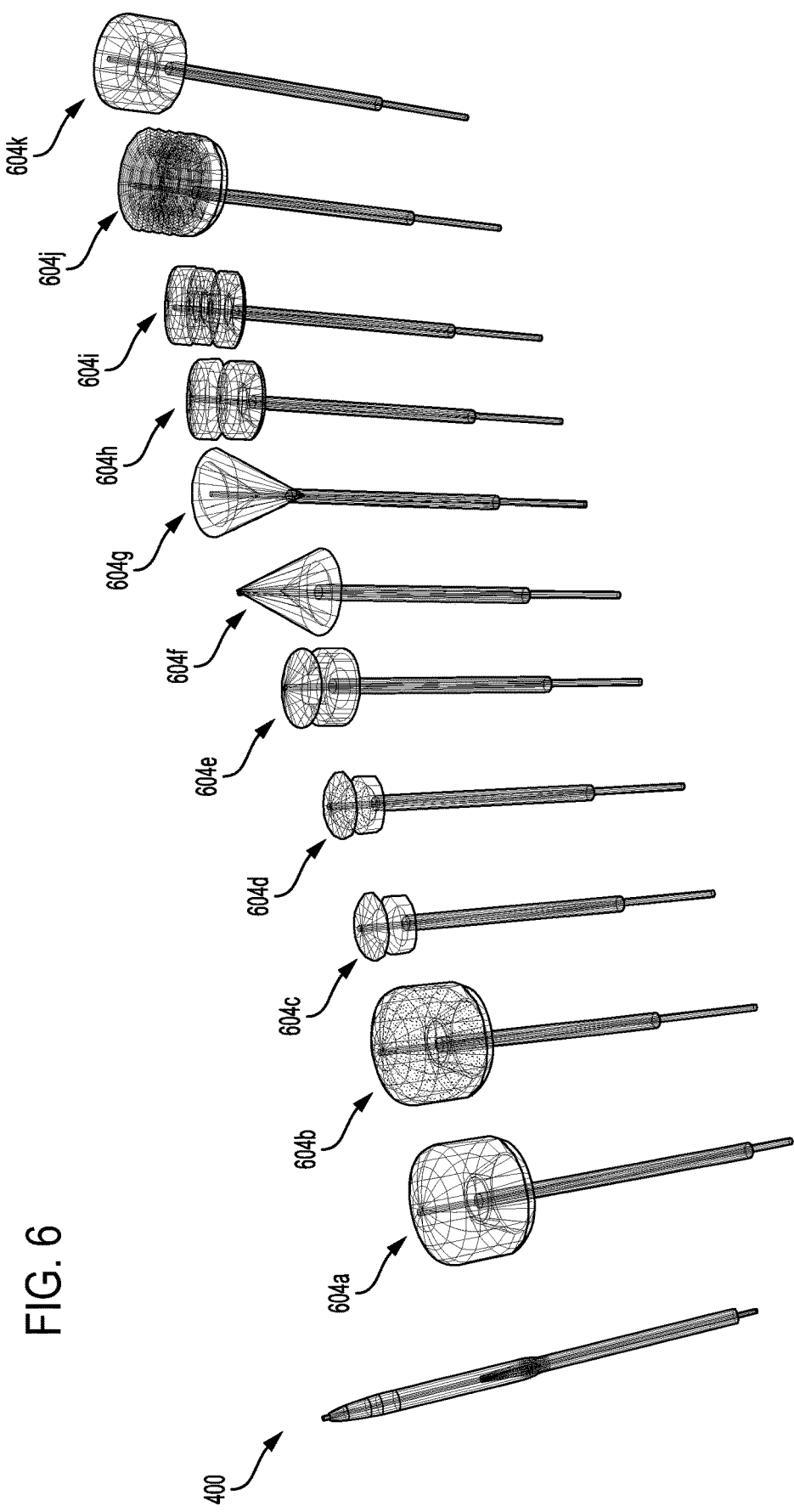
FIG. 6 illustrates exemplary guide wire configurations, according to some implementations of the current subject matter.

FIG. 6 illustrates exemplary geometries 604a-k of the guide wire system 400 (as shown in FIG. 4 and at the left-most diagram in FIG. 6). Such exemplary geometries can provide additional friction when the system 400 is anchored at the anchoring location. The geometries can include, but are not limited to a ball or a plug 604a, a covered ball 604b, a plug with a waist 604c, a covered plug with a waist 604d, a plug with a waist and a cylinder 604e, a cone 604f, an inverted cone 604g (and/or a similar configuration that can be used as a suction cup in combination with a vacuum in order to stabilize the guide wire at a specific anchoring position), a dual accordion 604h, a triple accordion 604i, a multiple-accordion structure 604j, a torus 604k, and/or any other shapes and/or any combination thereof.

Figure 7A:
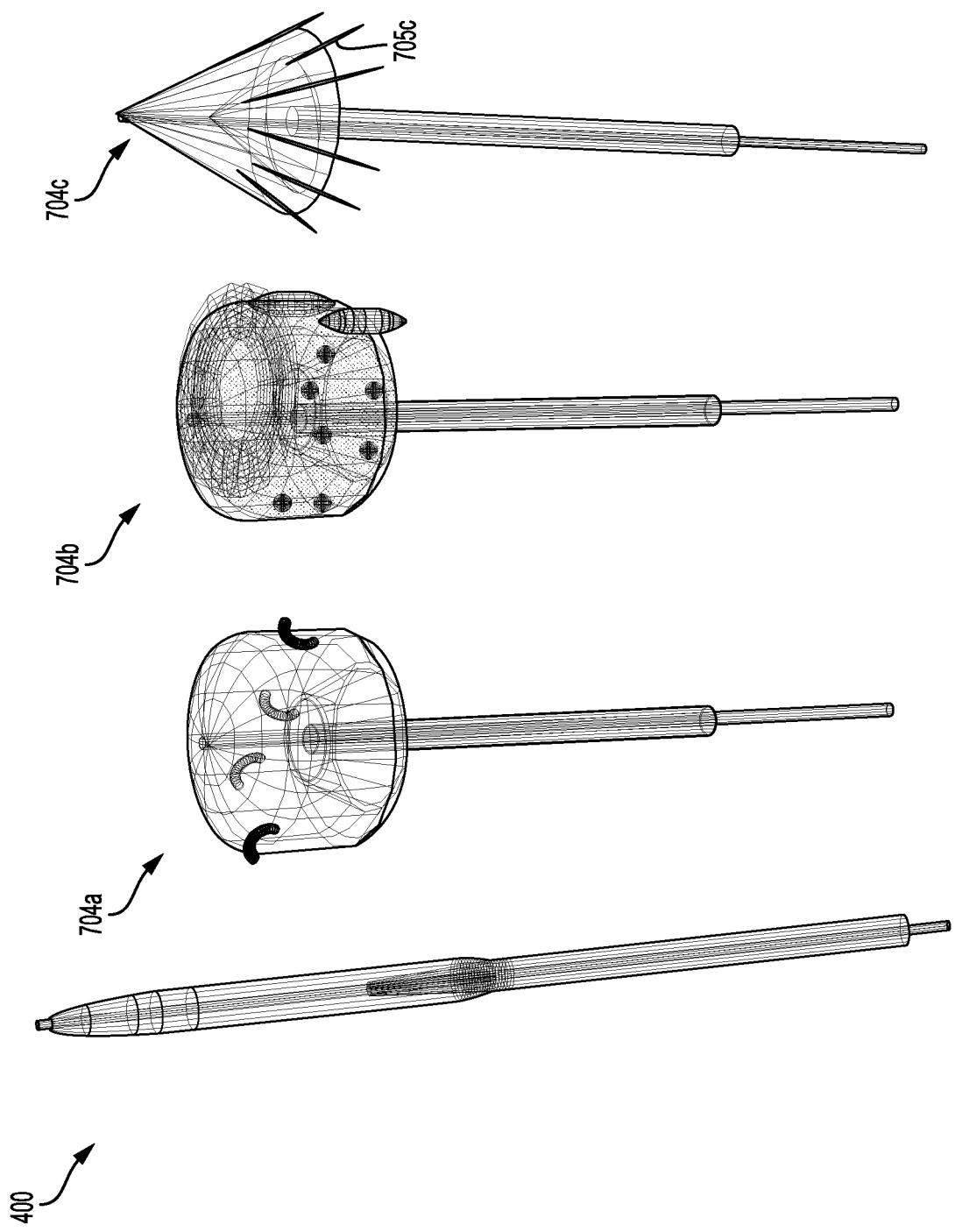
FIG. 7a illustrates exemplary guide wire configurations, according to some implementations of the current subject matter.

FIG. 7a illustrates additional securing mechanisms 704a-c of the guide wire system 400 (as shown in FIG. 4 and at the left-most diagram in FIG. 7a) that can provide additional friction to the system 400 at the anchoring location. Such mechanisms can include, but are not limited to hooks 704a-b, pins 704c (assuming the pins can be re-sheathed), noses, axial and/or circumferential ribs, rough surfaces, one or more hooks (e.g., similar to a harpoon-like hook), bars, loops, wings, etc. and/or any other mechanisms, and/or any combination thereof. In some implementations, the mechanisms 704, as shown in FIG. 7a, can be used to perform static anchoring of the guide wire.

In some alternate implementations, the current subject matter can perform dynamic anchoring of the guide wire. For example, dynamic anchoring can be performed by replacing the pins 705c with one or more fluid jets and/or any other mechanisms. For this purpose, the hollow interior of the guide wire can be partially and/or completely filled with fluid (e.g., saline, contrast fluid, etc.), gas, and/or any other suitable substance (where at least a portion of the hollow interior is occupied by the core wire). The substance can be used for the purposes of performing a substance injection. In some exemplary implementations, the pins 705c can be replaced with specifically-designed nozzles that can project the substance backwards toward the point of insertion of the guide wire. Once the anchoring mechanism is activated, the nozzles can begin expunging the substance (e.g., at a predetermined pressure, flow volume, etc.), thereby retaining the guide wire tip in a particular position regardless of movement of fluids at the target location (e.g., the blood stream flow). Alternatively, the nozzles (which can have directional capabilities) can be used to advance the guide wire tip in a desired direction (e.g., forward toward a target location, backward away from the target location, realign the guidewire tip, and/or perform movement in any other desired direction)

Figure 7B:
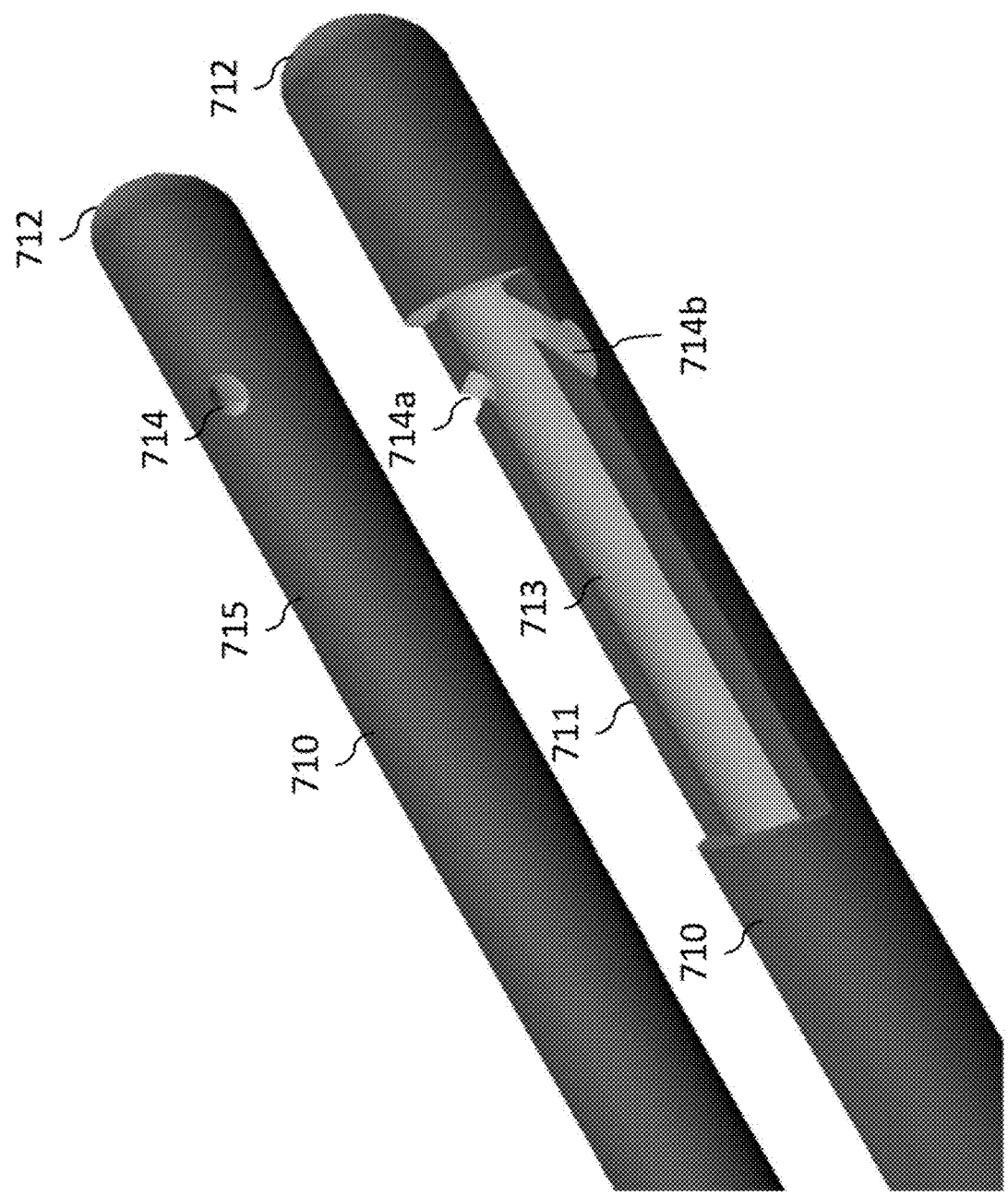
FIG. 7b illustrates an exemplary guide wire that can be dynamically positioned, according to some implementations of the current subject matter.

FIG. 7b illustrates an exemplary guide wire 710 having one or more directional tip orifices and/or nozzles 714. The bottom portion of FIG. 7b illustrates further details of the guide wire 710 (shown in the top portion of FIG. 7b), whereby a portion 711 has been cut out to show further details. Similar to the discussion above, the guide wire 710 can include a housing 715 having a distal end or tip 712 and a hollow interior (and/or lumen) 713 contained within the housing 715. The hollow interior can be configured for insertion of a core wire (not shown in FIG. 7b) and/or any other substances, as discussed above. The housing 715 can further include one or more nozzles 714 (a, b). The nozzles 714 can be openings in the housing 715 that can allow expungement of substance from the interior portion 713. The nozzles 714 can be positioned at any location on the guide wire 710 and can be oriented in any desired direction (alternatively, the nozzles can be dynamically oriented, and/or fixed in a particular direction). Further, the guide wire 710 can have any number of nozzles 714 having any desired shape (e.g., circle, square, rectangular, oval, irregular, etc.). In some implementations, the nozzles 714 can be positioned symmetrically and/or asymmetrically about the center of the housing 715. Upon advancement of the substance through the interior portion 713 and expungement of the substances through the nozzles, one or more nozzles 714 can be configured to steer the tip 712 of the guide wire in any desired direction (e.g., the substance being expunged from a nozzle 714 can be configured to move the tip 712 in an opposite direction of the flow of the substance from the nozzle 714). In some implementations, the nozzles 714 can be opened and/or closed, as desired, to more precisely configure direction of movement of the tip 712. Use of the nozzles can be combined with rotation and/or translation motion(s) of the guide wire, thereby allowing every point within a vessel/hollow organ to be reached.

In some exemplary implementations, the nozzles 714 can be activated and/or deactivated (e.g., opened/closed) and/or orientated in a particular direction using one or more valves. Nozzle opening, closure and/or steering can also be achieved by moving a core wire in and/or out of a channel connecting the nozzle to the inner lumen. Further, control of nozzle movement, orientation, etc., can be accomplished using various forms of pressure, electrical current, galvanic, etc.

In some exemplary implementations, the current subject matter can also similarly perform dynamic steering of a catheter which may or may not serve as a guiding structure for device insertion and/or other therapeutic and/or diagnostic procedures.

Figure 8:
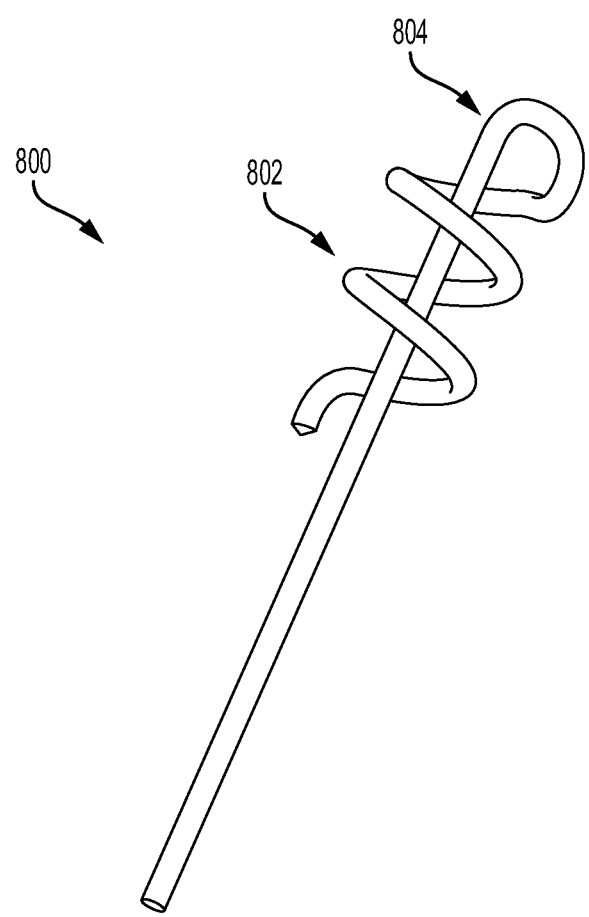
FIG. 8 illustrates exemplary inverted guide wire configuration, according to some implementations of the current subject matter.
Figure 9:
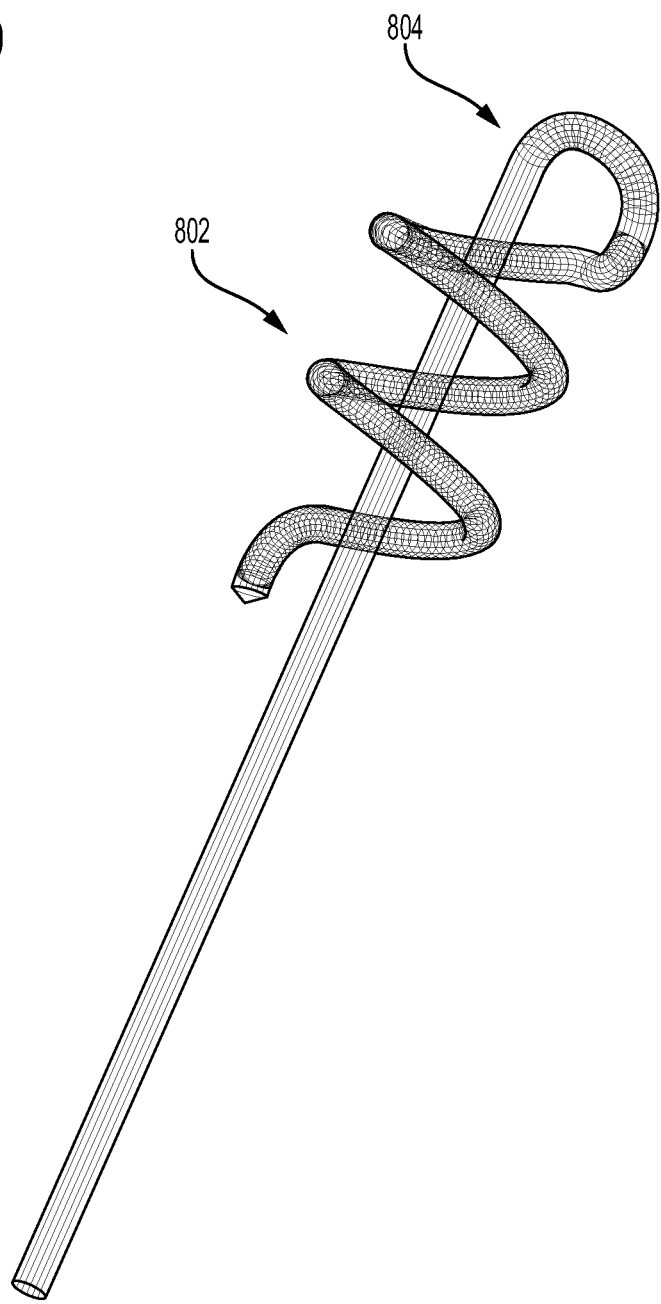
FIG. 9 illustrates another exemplary inverted guide wire configuration, according to some implementations of the current subject matter.

FIGS. 8 and 9 illustrate exemplary inverted guide wires 800, according to some implementations of the current subject matter. The guide wire 800 can have an anchoring section 802, whereby the guide wire can be inserted through an interior of the anchoring section 802 (e.g., angle α can be 180°). The inverted guide wire 800 can provide additional resistive friction force that can prevent dislodging of the guide wire from the anchoring location. Additionally, the anchoring location can be the same as the device implantation location.

Figure 14A:
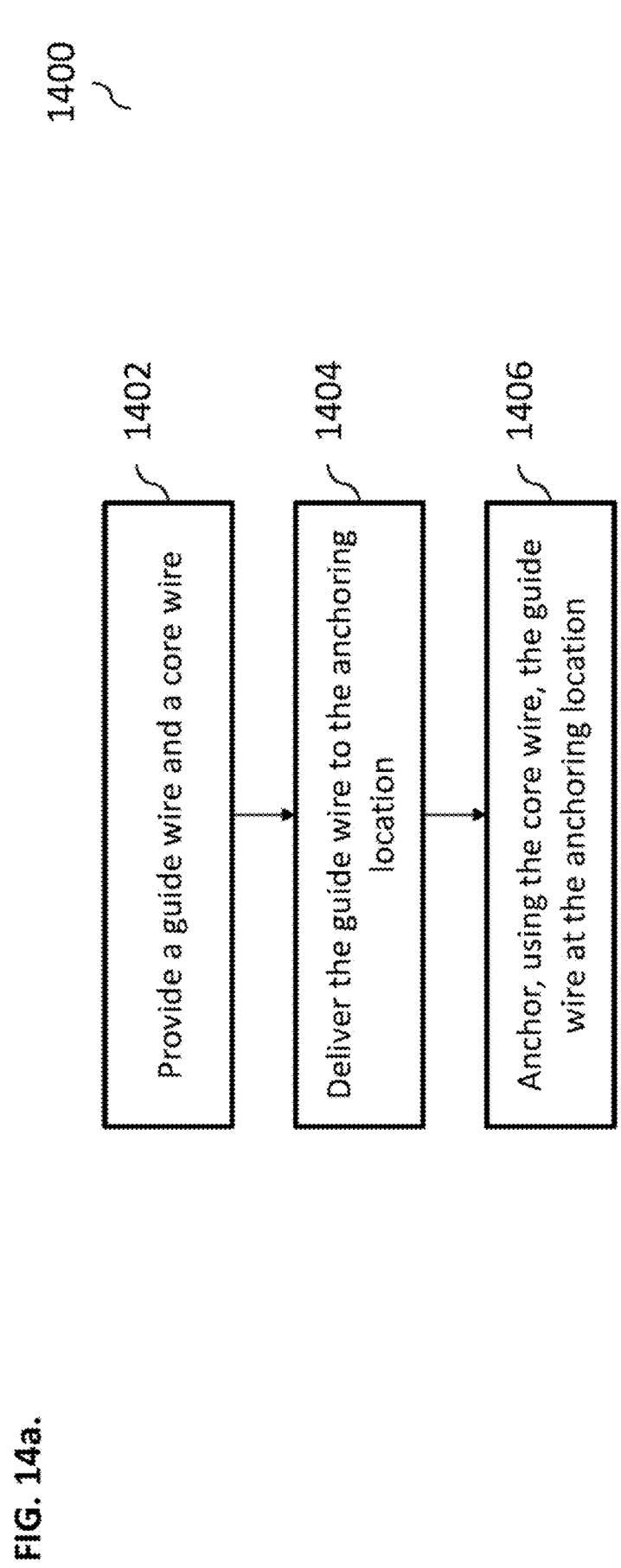
FIGS. 14a-b illustrate exemplary methods, according to some implementations of the current subject matter.

FIG. 14*a* illustrates an exemplary method 1400 for using the guide wire (and/or catheter) discussed above, according to some implementations of the current subject matter. At 1402, a guide wire and a core wire can be provided. The guide wire can have a distal end, a hollow interior (whereby the guide wire may or may not have a hollow interior), and an anchoring mechanism positioned proximate to the distal end of the guide wire. The core wire can be configured to be slidably inserted into the hollow interior of the guide wire. Upon insertion, the core wire can be configured to actuate the anchoring mechanism to anchor the guide wire at an anchoring location. At 1404, the guide wire can be delivered to the anchoring location. At 1406, the guide wire can be anchored at the anchoring location using the core wire.

In some implementations, the current subject matter can include one or more of the following optional features. The core wire can include a distal end, where the distal end of the core wire can be configured to be positioned proximate to the anchoring location of the guide wire and proximate to the distal end of the guide wire.

In some implementations, the guide wire can include a tip at the distal end of the guide wire. The distal end of the core wire can be configured to be coupled to at least one of the distal end guide wire and the tip of guide wire.

In some implementations, the core wire can be configured to deactivate the anchoring mechanism for removing of the guidewire from the anchoring location. The core wire can include an actuation mechanism disposed at a proximate end of the core wire. The actuation mechanism can be configured to perform activation and deactivation of the anchoring mechanism.

In some implementations, the anchoring location can include at least one of the following: a target location for delivery of a medical device or a procedure, a location proximate to the target location, and any combination thereof. The anchoring mechanism can include at least one of a contracted state and an expanded state. In the contracted state, the guide wire can be configured for at least one of an insertion into the target location and removal of the guide wire from the target location. In the expanded state, the anchoring mechanism can be configured to be activated and can be further configured to secure the guide wire at at least one of proximate to the target location and at the target location. Further, in the expanded state, a first section of the guide wire extending from a proximate end of the guide wire to a second section of the guide wire that connects to the anchoring mechanism can be configured to be tensioned.

In some implementations, the anchoring mechanism can include at least one of the following: a coil, an angle, a Z-shape, a zig-zag shape, and any combination thereof.

In some implementations, the anchoring mechanism can be at least one of a two-dimensional anchoring mechanism configured to anchor the guide wire at the anchoring location in at least two dimensions, and a three-dimensional anchoring mechanism configured to anchor the guide wire at the anchoring location in at least three dimensions.

In some implementations, the anchoring mechanism can include at least one of the following: a basket, a ball, an ovoid, a diabolo, a cylinder, a cone, an inverted cone, a pyramid, a screw, one or several directional nozzles, a suction cup and/or any other shapes, and/or any combinations thereof.

In some implementations, the anchoring mechanism can include at least one of the following: a ball or a plug, a covered ball, a plug with a waist, a covered plug with a waist, a cone, an inverted cone, a dual accordion, a triple accordion, a multiple-accordion structure, a torus, and/or any other shapes, and/or any combinations thereof.

In some implementations, the anchoring mechanism can include at least one of the following: a pin, a hook, a balloon, and/or any combinations thereof.

In some implementations, the guide wire can include a navigation section, the anchoring mechanism, a device transfer section, a device implantation section, and a steering section. The navigation section can be configured to be located proximate to the distal end of the guide wire and is further configured to navigate the guide wire to at least a target location. The anchoring mechanism can be configured to be located adjacent to the navigation section. The device transfer section can be configured to be located adjacent to the anchoring mechanism and can be further configured to transfer a medical device to the device implantation section for implantation. The medical device can be configured to be delivered over the guide wire to the target location. The device implantation section can be configured to be located adjacent to the device transfer section and can be further configured for implantation of the medical device at the target location. The steering section can be configured to be located proximate to the proximate end of the guide wire.

In some implementations, upon actuation of the anchoring mechanism, the guide wire can be configured to form at least one angle between the anchoring section and the device implantation section. The anchoring mechanism can be configured to anchor the guide wire at the anchoring location using at least one of the following: a friction fit, a form fit, an active fixation, a permanent fixation, a temporary fixation, and any combination thereof. The anchoring mechanism can be also configured to anchor the guide wire at the anchoring location using at least one of the following: an automatic anchoring, a manual anchoring, and any combination thereof.

In some implementations, the anchoring mechanism can include at least one steering mechanism for at least one of: dynamically moving, steering, positioning, stabilization, and anchoring of the guide wire to at least the anchoring location. The steering mechanism can include at least one nozzle configured to provide a conduit between the hollow interior of the guide wire and an exterior of the guide wire. At least one nozzle can be configured to be actuated using at least one of: the core wire and a pressure applied from the hollow interior of the guide wire, wherein the pressure is applied using at least one substance. Upon actuation, the nozzle can be configured to expunge the at least one substance from the hollow interior of the guide wire to perform at least one of: movement, steering, positioning, stabilization, and anchoring of the guide wire. The nozzle can be configured to be positioned proximate to the distal end of the guide wire. The substance can include at least one of the following: a fluid substance, a gaseous substance, an amorphous substance, a solid substance, and any combination thereof.

Figure 14B:
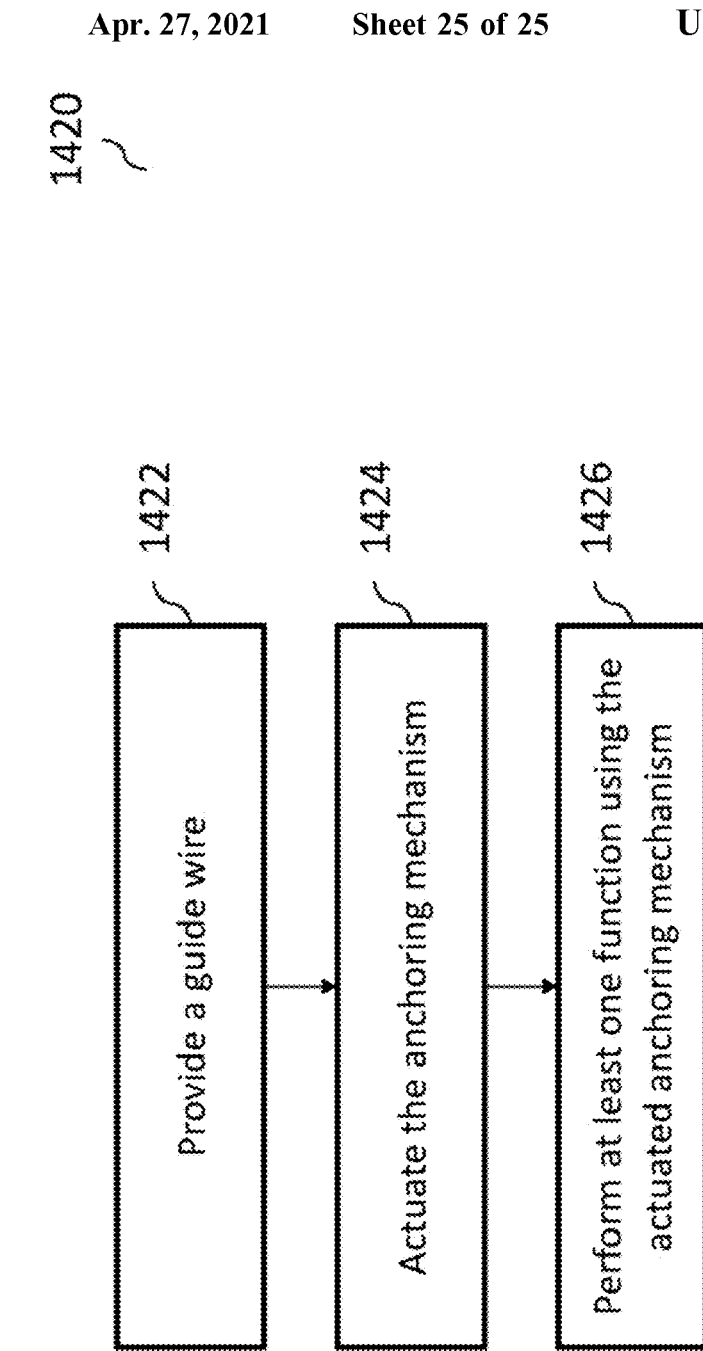

FIG. 14b illustrates another exemplary method 1420 for using a guide wire (such as the guide wire described above), according to some implementations of the current subject matter. At 1422, a guide wire (e.g., a guide wire as shown in FIGS. 1d, 7b, which may or may not require a core wire for anchoring, steering, movement, stabilization, etc.) having a distal end, a hollow lumen (e.g., a hollow interior as described above), and an anchoring mechanism positioned proximate to the distal end of the guide wire. At 1424, the anchoring mechanism can be anchored by pressurizing at least one substance inside the hollow lumen (e.g., as discussed above with regard to FIG. 7b). At 1426, using the actuated anchoring mechanism, at least one of the following functions can be performed: advancement of the guide wire in a desired direction (e.g., a target location, an anchoring location, a specific location within a bodily organ, etc.), anchoring of the guide wire at an anchoring location (as discussed above), steering of the guide wire in a desired direction (e.g., toward a target location, an anchoring location, a specific location within a bodily organ, etc.), positioning of the guide wire at a predetermined location (e.g., a target location, an anchoring location, a specific location within a bodily organ, etc.), stabilizing the guide wire at a predetermined location (e.g., a target location, an anchoring location, a specific location within a bodily organ, etc.), and any combination thereof.

In some implementations, the current subject matter can include one or more of the following optional features (in addition to the features described herein). The anchoring mechanism can include at least one nozzle (e.g., as shown in FIG. 7b) configured to provide a conduit between the hollow lumen of the guide wire and an exterior of the guide wire. The nozzle can be configured to be actuated using at least one of: a core wire and a pressure applied from the hollow lumen of the guide wire, wherein the pressure is applied using at least one substance. Upon actuation, the nozzle can be configured to expunge the substance from the hollow interior of the guide wire to perform at least one of: movement, steering, positioning, stabilization, and anchoring of the guide wire. The substance can include at least one of the following: a fluid substance (e.g., saline, therapeutic fluid, etc.), a gaseous substance (e.g., air, gas, etc.), an amorphous substance (e.g., a combination of fluids, gases, solids, etc.), a solid substance (e.g., a metal, etc.), and any combination thereof. The nozzle can be configured to be positioned proximate to the distal end of the guide wire. In some implementations, the guide wire can be a catheter for performing at least one of a diagnostic procedure and a therapeutic procedure.

In some implementations, the guide wire can be a catheter configured to be at least one of: dynamically moved, steered, positioned, stabilized, and anchored at a predetermined location for performing at least one diagnostic procedure and a therapeutic procedure.

In some implementations, the current subject matter relates to a method (e.g., similar to a method shown in FIG. 14b) of using a guide wire (such as a guide wire shown in FIG. 2). The method can include providing a guide wire having a distal end and an anchoring mechanism positioned proximate to the distal end of the guide wire. The anchoring mechanism can have a first configuration (e.g., a contracted state, as discussed above) for delivery of the guide wire to an anchoring location, and a second configuration (e.g., an expanded state, as discussed above) for anchoring of the guide wire at the anchoring location. The first configuration can have at least one dimension smaller than at least one dimension of the anchoring location (e.g., the guide wire can be stretched for delivery of the guide wire and hence be smaller than a diameter of a vessel to where it is being delivered). The second configuration can have at least one dimension larger (e.g., as shown in FIG. 2, in the expanded state, the guide wire have its anchoring section be larger than a diameter of a vessel where the guide wire is being delivered to) than at least one dimension of the anchoring location. The method can also include delivering the guide wire to the anchoring location, actuating the anchoring mechanism, where the anchoring mechanism can be configured to assume the second configuration, and anchoring the guide wire at the anchoring location.

In some implementations, the current subject matter can include one or more of the following optional features. The anchoring location can include at least one of the following: a target location for delivery of a medical device or a procedure, a location proximate to the target location, and any combination thereof.

In some implementations, the first configuration can correspond to an expanded state of the guide wire, where, in the expanded state, a first section of the guide wire extending from a proximate end of the guide wire to a second section of the guide wire that connects to the anchoring mechanism is configured to be tensioned.

In some implementations, the anchoring mechanism can include at least one of the following: a coil, an angle, a Z-shape, a zig-zag shape, and any combination thereof. The anchoring mechanism can be at least one of a two-dimensional anchoring mechanism configured to anchor the guide wire at the anchoring location in at least two dimensions, and a three-dimensional anchoring mechanism configured to anchor the guide wire at the anchoring location in at least three dimensions. The anchoring mechanism can include at least one of the following: a basket, a ball, an ovoid, a diabolo, a cylinder, a cone, an inverted cone, a pyramid, a screw, one or several directional nozzles, a suction cup and/or any other shapes, and/or any combinations thereof. The anchoring mechanism can include at least one of the following: a ball or a plug, a covered ball, a plug with a waist, a covered plug with a waist, a cone, an inverted cone, a dual accordion, a triple accordion, a multiple-accordion structure, a torus, and/or any other shapes, and/or any combinations thereof. The anchoring mechanism can also include at least one of the following: a pin, a hook, a balloon, and/or any combinations thereof.

In some implementations, upon actuation of the anchoring mechanism, the guide wire can be configured to form at least one angle.

In some implementations, the anchoring mechanism can be configured to anchor the guide wire at the anchoring location using at least one of the following: a friction fit, a form fit, an active fixation, a permanent fixation, a temporary fixation, and any combination thereof. The anchoring mechanism can be further configured to anchor the guide wire at the anchoring location using at least one of the following: an automatic anchoring, a manual anchoring, and any combination thereof.

In some implementations, a sheathing device (e.g., a catheter, and/or any other sheathing device, etc.) can be provided to sheath the guide wire for delivery of the guide wire to the anchoring location in the first configuration. Upon removal of the sheathing device, the guide wire can be configured to assume the second configuration.

As used herein, the term "user" can refer to any entity including a person or a computer.

Although ordinal numbers such as first, second, and the like can, in some situations, relate to an order; as used in this document ordinal numbers do not necessarily imply an order. For example, ordinal numbers can be merely used to distinguish one item from another. For example, to distinguish a first event from a second event, but need not imply any chronological ordering or a fixed reference system (such that a first event in one paragraph of the description can be different from a first event in another paragraph of the description).

The foregoing description is intended to illustrate but not to limit the scope of the invention, which is defined by the scope of the appended claims. Other implementations are within the scope of the following claims.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and sub-combinations of the disclosed features and/or combinations and sub-combinations of several further features disclosed above. In addition, the logic flows depicted in the accompanying figures and/or described herein do not necessarily require the particular order shown, or sequential order, to achieve desirable results. Other implementations can be within the scope of the following claims.

What is claimed is:

1. A device, comprising:
a guide wire having a distal end, a hollow interior, and an anchoring mechanism positioned proximate to the distal end of the guide wire; and
a core wire configured to be slidably inserted into the hollow interior of the guide wire and, upon insertion, configured to actuate the anchoring mechanism to anchor the guide wire at an anchoring location;
wherein
the anchoring mechanism includes at least one steering mechanism for at least one of: dynamically moving, steering, positioning, stabilization, and anchoring of the guide wire to at least the anchoring location;
the steering mechanism includes at least one nozzle configured to provide a conduit between the hollow interior of the guide wire and an exterior of the guide wire;
the at least one nozzle is configured to be actuated using at least one of: the core wire and a pressure applied from the hollow interior of the guide wire, wherein the pressure is applied using at least one substance;
upon actuation, the at least one nozzle is configured to expunge the at least one substance from the hollow interior of the guide wire to perform at least one of: movement, steering, positioning, stabilization, and anchoring of the guide wire;
the at least one substance includes at least one of the following: a fluid substance, a gaseous substance, an amorphous substance, a solid substance, and any combination thereof;
the guide wire includes a tip at the distal end of the guide wire;
the distal end of the core wire is configured to be coupled to at least one of the distal end of the guide wire and the tip of the guide wire.

2. The device according to claim 1, wherein the core wire includes a distal end, the distal end of the core wire is configured to be positioned proximate to the anchoring location of the guide wire and proximate to the distal end of the guide wire.

3. The device according to claim 1, wherein the core wire is configured to deactivate the anchoring mechanism for removing of the guidewire from the anchoring location.

4. The device according to claim 3, wherein the core wire includes an actuation mechanism disposed at a proximate end of the core wire, the actuation mechanism is configured to perform activation and deactivation of the anchoring mechanism.

5. The device according to claim 1, wherein the anchoring location includes at least one of the following: a target location for delivery of a medical device or a procedure, a location proximate to the target location, and any combination thereof.

6. The device according to claim 5, wherein the anchoring mechanism includes at least one of a contracted state and an expanded state, wherein
in the contracted state, the guide wire is configured for at least one of an insertion into the target location and removal of the guide wire from the target location;
in the expanded state, the anchoring mechanism is configured to be activated and is further configured to secure the guide wire at at least one of proximate to the target location and at the target location.

7. The device according to claim 6, wherein in the expanded state, a first section of the guide wire extending from a proximate end of the guide wire to a second section of the guide wire that connects to the anchoring mechanism is configured to be tensioned.

8. The device according to claim 1, wherein the anchoring mechanism is configured to change an anchoring section of the guide wire into at least one of the following: a coil, an angle, a Z-shape, a zig-zag shape, and any combination thereof.

9. The device according to claim 1, wherein the anchoring mechanism is at least one of a two-dimensional anchoring mechanism configured to anchor the guide wire at the anchoring location in at least two dimensions, and a three-dimensional anchoring mechanism configured to anchor the guide wire at the anchoring location in at least three dimensions.

10. The device according to claim 1, wherein the guide wire includes a navigation section, the anchoring mechanism, a device transfer section, a device implantation section, and a steering section;
wherein
the navigation section is configured to be located proximate to the distal end of the guide wire and is further configured to navigate the guide wire to at least a target location;
the anchoring mechanism is configured to be located adjacent to the navigation section;
the device transfer section is configured to be located adjacent to the anchoring mechanism and is further configured to transfer a medical device to the device implantation section for implantation, wherein the medical device is configured to be delivered over the guide wire to the target location;
the device implantation section is configured to be located adjacent to the device transfer section and is further configured for implantation of the medical device at the target location; and
the steering section is configured to be located proximate to the proximate end of the guide wire.

11. The device according to claim 10, wherein upon actuation of the anchoring mechanism, the guide wire is configured to form at least one angle between an anchoring section of the guide wire and the device implantation section.

12. The device according to claim 11, wherein the anchoring mechanism is configured to anchor the guide wire at the anchoring location using at least one of the following: a friction fit, a form fit, an active fixation, a permanent fixation, a temporary fixation, and any combination thereof.

13. The device according to claim 11, wherein the anchoring mechanism is configured to anchor the guide wire at the anchoring location using at least one of the following: an automatic anchoring, a manual anchoring, and any combination thereof.

14. The device according to claim 1, wherein the at least one nozzle is configured to be positioned proximate to the distal end of the guide wire.

15. The device according to claim 14, wherein the guide wire is a catheter configured to be at least one of: dynamically moved, steered, positioned, stabilized, and anchored at a predetermined location for performing at least one of a diagnostic procedure and a therapeutic procedure.

16. A method comprising:
providing
a guide wire having a distal end, a hollow interior, and an anchoring mechanism positioned proximate to the distal end of the guide wire; and
a core wire configured to be slidably inserted into the hollow interior of the guide wire and, upon insertion, configured to actuate the anchoring mechanism to anchor the guide wire at an anchoring location, wherein
the anchoring mechanism includes at least one steering mechanism for at least one of: dynamically moving, steering, positioning, stabilization, and anchoring of the guide wire to at least the anchoring location;

the steering mechanism includes at least one nozzle configured to provide a conduit between the hollow interior of the guide wire and an exterior of the guide wire;
the at least one nozzle is configured to be actuated using at least one of: the core wire and a pressure applied from the hollow interior of the guide wire, wherein the pressure is applied using at least one substance;
upon actuation, the at least one nozzle is configured to expunge the at least one substance from the hollow interior of the guide wire to perform at least one of: movement, steering, positioning, stabilization, and anchoring of the guide wire;
the at least one substance includes at least one of the following: a fluid substance, a gaseous substance, an amorphous substance, a solid substance, and any combination thereof;
the guide wire includes a tip at the distal end of the guide wire;
the distal end of the core wire is configured to be coupled to at least one of the distal end of the guide wire and the tip of the guide wire.
delivering the guide wire to the anchoring location; and
anchoring, using the core wire, the guide wire at the anchoring location.

17. The method according to claim 16, wherein the core wire includes a distal end, the distal end of the core wire is configured to be positioned proximate to the anchoring location of the guide wire and proximate to the distal end of the guide wire.

18. The method according to claim 16, wherein the core wire is configured to deactivate the anchoring mechanism for removing of the guidewire from the anchoring location.

19. The method according to claim 18, wherein the core wire includes an actuation mechanism disposed at a proximate end of the core wire, the actuation mechanism is configured to perform activation and deactivation of the anchoring mechanism.

20. The method according to claim 16, wherein the anchoring location includes at least one of the following: a target location for delivery of a medical device or a procedure, a location proximate to the target location, and any combination thereof.

21. The method according to claim 20, wherein the anchoring mechanism includes at least one of a contracted state and an expanded state, wherein
in the contracted state, the guide wire is configured for at least one of an insertion into the target location and removal of the guide wire from the target location;
in the expanded state, the anchoring mechanism is configured to be activated and is further configured to secure the guide wire at at least one of proximate to the target location and at the target location.

22. The method according to claim 21, wherein in the expanded state, a first section of the guide wire extending from a proximate end of the guide wire to a second section of the guide wire that connects to the anchoring mechanism is configured to be tensioned.

23. The method according to claim 16, wherein the anchoring mechanism is configured to change an anchoring section of the guide wire into at least one of the following: a coil, an angle, a Z-shape, a zig-zag shape, and any combination thereof.

24. The method according to claim 16, wherein the anchoring mechanism is at least one of a two-dimensional anchoring mechanism configured to anchor the guide wire at the anchoring location in at least two dimensions, and a three-dimensional anchoring mechanism configured to anchor the guide wire at the anchoring location in at least three dimensions.

25. The method according to claim 16, wherein the guide wire includes a navigation section, the anchoring mechanism, a device transfer section, a device implantation section, and a steering section;
wherein
the navigation section is configured to be located proximate to the distal end of the guide wire and is further configured to navigate the guide wire to at least a target location;
the anchoring mechanism is configured to be located adjacent to the navigation section;
the device transfer section is configured to be located adjacent to the anchoring mechanism and is further configured to transfer a medical device to the device implantation section for implantation, wherein the medical device is configured to be delivered over the guide wire to the target location;
the device implantation section is configured to be located adjacent to the device transfer section and is further configured for implantation of the medical device at the target location; and
the steering section is configured to be located proximate to the proximate end of the guide wire.

26. The method according to claim 25, wherein upon actuation of the anchoring mechanism, the guide wire is configured to form at least one angle between an anchoring section of the guide wire and the device implantation section.

27. The method according to claim 26, wherein the anchoring mechanism is configured to anchor the guide wire at the anchoring location using at least one of the following: a friction fit, a form fit, an active fixation, a permanent fixation, a temporary fixation, and any combination thereof.

28. The method according to claim 26, wherein the anchoring mechanism is configured to anchor the guide wire at the anchoring location using at least one of the following: an automatic anchoring, a manual anchoring, and any combination thereof.

29. The method according to claim 16, wherein the at least one nozzle is configured to be positioned proximate to the distal end of the guide wire.

30. The method according to claim 29, wherein the guide wire is a catheter configured to be at least one of: dynamically moved, steered, positioned, stabilized, and anchored at a predetermined location for performing at least one of a diagnostic procedure and a therapeutic procedure.

31. A device, comprising:
a guide wire having a distal end and an anchoring mechanism positioned proximate to the distal end of the guide wire; and
the anchoring mechanism having a first configuration for delivery of the guide wire to an anchoring location, and a second configuration for anchoring of the guide wire at the anchoring location, the first configuration having at least one dimension smaller than at least one dimension of the anchoring location and the second configuration having at least one dimension larger than at least one dimension of the anchoring location;
upon actuation, the anchoring mechanism is configured to assume the second configuration and anchor the guide wire at the anchoring location;
wherein
the anchoring mechanism includes at least one steering mechanism for at least one of: dynamically moving, steering, positioning, stabilization, and anchoring of the guide wire to at least the anchoring location;
the steering mechanism includes at least one nozzle configured to provide a conduit between the hollow interior of the guide wire and an exterior of the guide wire;
the at least one nozzle is configured to be actuated using at least one a pressure applied from the hollow interior of the guide wire, wherein the pressure is applied using at least one substance;
upon actuation, the at least one nozzle is configured to expunge the at least one substance from the hollow interior of the guide wire to perform at least one of: movement, steering, positioning, stabilization, and anchoring of the guide wire;
the at least one substance includes at least one of the following: a fluid substance, a gaseous substance, an amorphous substance, a solid substance, and any combination thereof;
the guide wire includes a tip at the distal end of the guide wire;
the distal end of the core wire is configured to be coupled to at least one of the distal end of the guide wire and the tip of the guide wire.

32. The device according to claim 31, wherein the anchoring location includes at least one of the following: a target location for delivery of a medical device or a procedure, a location proximate to the target location, and any combination thereof.

33. The device according to claim 32, wherein the first configuration corresponds to an expanded state of the guide wire, wherein, in the expanded state, a first section of the guide wire extending from a proximate end of the guide wire to a second section of the guide wire that connects to the anchoring mechanism is configured to be tensioned.

34. The device according to claim 31, wherein the anchoring mechanism is configured to change an anchoring section of the guide wire into at least one of the following: a coil, an angle, a Z-shape, a zig-zag shape, and any combination thereof.

35. The device according to claim 31, wherein the anchoring mechanism is at least one of a two-dimensional anchoring mechanism configured to anchor the guide wire at the anchoring location in at least two dimensions, and a three-dimensional anchoring mechanism configured to anchor the guide wire at the anchoring location in at least three dimensions.

36. The device according to claim 31, wherein upon actuation of the anchoring mechanism, the guide wire is configured to form at least one angle.

37. The device according to claim 36, wherein the anchoring mechanism is configured to anchor the guide wire at the anchoring location using at least one of the following: a friction fit, a form fit, an active fixation, a permanent fixation, a temporary fixation, and any combination thereof.

38. The device according to claim 37, wherein the anchoring mechanism is configured to anchor the guide wire at the anchoring location using at least one of the following: an automatic anchoring, a manual anchoring, and any combination thereof.

39. The device according to claim 31, further comprising a sheathing device configured to sheath the guide wire for delivery of the guide wire to the anchoring location in the first configuration;

wherein, upon removal of the sheathing device, the guide wire is configured to assume the second configuration.

40. A method, comprising:

providing
- a guide wire having a distal end and an anchoring mechanism positioned proximate to the distal end of the guide wire; and
- the anchoring mechanism having a first configuration for delivery of the guide wire to an anchoring location, and a second configuration for anchoring of the guide wire at the anchoring location, the first configuration having at least one dimension smaller than at least one dimension of the anchoring location and the second configuration having at least one dimension larger than at least one dimension of the anchoring location;
  - delivering the guide wire to the anchoring location, wherein the anchoring mechanism includes at least one steering mechanism for at least one of: dynamically moving, steering, positioning, stabilization, and anchoring of the guide wire to at least the anchoring location;
  - the steering mechanism includes at least one nozzle configured to provide a conduit between the hollow interior of the guide wire and an exterior of the guide wire;
  - the at least one nozzle is configured to be actuated using at least one a pressure applied from the hollow interior of the guide wire, wherein the pressure is applied using at least one substance;
  - upon actuation, the at least one nozzle is configured to expunge the at least one substance from the hollow interior of the guide wire to perform at least one of: movement, steering, positioning, stabilization, and anchoring of the guide wire:
  - the at least one substance includes at least one of the following: a fluid substance, a gaseous substance, an amorphous substance, a solid substance, and any combination thereof;
- the guide wire includes a tip at the distal end of the guide wire;
- the distal end of the core wire is configured to be coupled to at least one of the distal end of the guide wire and the tip of the guide wire.

actuating the anchoring mechanism, wherein the anchoring mechanism is configured to assume the second configuration; and anchoring the guide wire at the anchoring location.

* * * * *